US007039468B2

(12) United States Patent
Freed et al.

(10) Patent No.: US 7,039,468 B2

(45) Date of Patent: May 2, 2006

(54) METHOD AND APPARATUS FOR TREATING OROPHARYNGEAL DISORDERS WITH ELECTRICAL STIMULATION

(75) Inventors: Marcy L. Freed, Pepper Pike, OH (US); Leonard A. Freed, Kailua, HI (US); Michael O. Christian, Beachwood, OH (US); Howard Tucker, Cleveland Heights, OH (US); Bernard Kotton, Beachwood, OH (US); Erol M. Beytas, Beachwood, OH (US); Ed Dunlay, Hixson, TN (US); Tim Kretschmer, Wabasha, MN (US); Marie Asmar, Richmond Heights, OH (US)

(73) Assignee: ESD Limited Liability Company, Marysville, WA (US)

( * ) Notice: Subject to any disclaimer, the term of this patent is extended or adjusted under 35 U.S.C. 154(b) by 469 days.

(21) Appl. No.: 10/375,407

(22) Filed: Feb. 27, 2003

(65) Prior Publication Data

US 2004/0034396 A1 Feb. 19, 2004

Related U.S. Application Data

(63) Continuation-in-part of application No. 10/308,105, filed on Dec. 3, 2002, now abandoned, which is a continuation of application No. 09/757,804, filed on Jan. 11, 2001, now abandoned, which is a continuation of application No. 09/236,829, filed on Jan. 25, 1999, now Pat. No. 6,148,970, which is a continuation-in-part of application No. 08/956,448, filed on Oct. 23, 1997, now Pat. No. 5,987,351, which is a continuation of application No. 08/549,046, filed on Oct. 27, 1995, now Pat. No. 5,725,564.

(51) Int. Cl.
*A61N 1/04* (2006.01)

(52) U.S. Cl. ........................................ 607/72; 600/392

(58) Field of Classification Search .................. 607/72; 600/391, 392, 3

See application file for complete search history.

(56) References Cited

U.S. PATENT DOCUMENTS 3,277,892 A 10/1966 Tepper (Continued)

OTHER PUBLICATIONS

Arthur J. Miller, *Characteristics of the Swallowing Reflex Induced by Peripheral Nerve and Brain Stem Stimulation*; 1972; Experimental Neurology, pp. 210-222; vol. 34; Publisher: Academic Press, Inc.

(Continued)

*Primary Examiner*—Scott M. Getzow

(74) *Attorney, Agent, or Firm*—Chambliss, Bahner & Stophel, P.C.

(57) ABSTRACT

A simple, non-invasive method and apparatus for treating oropharyngeal disorders provides electrical stimulation to the oropharyngeal region of a patient. The apparatus includes an electrical neuromuscular stimulator that includes a pulse generator for generating a series of electrical pulses and a processor coupled to the pulse generator for controlling its operation. The apparatus also includes a first electrode and a second electrode, each of which includes a snap eyelet having a connector to which a lead wire may be attached, a conductive film and an adhesive and conductive gel layer that is adapted to be attached to the skin of the patient. The apparatus also includes at least one lead wire for attachment of the electrodes to the pulse generator and at least one adhesively backed tape overlay for securing the first and second electrodes to the skin of the patient. According to the method, the electrodes are placed on the skin of the patient's throat, and the electrodes are secured to the skin of the patient's throat by applying at least one adhesively backed tape overlay to the patient's skin over at least a portion of each of the electrodes. The lead wires are attached to the connectors of the snap eyelets of the electrodes and to the output jack of the pulse generator, and a series of electrical pulses is generated using the pulse generator so as to apply the series of electrical pulses to the patient's throat using the electrodes.

20 Claims, 14 Drawing Sheets

U.S. PATENT DOCUMENTS

| | | | |
|---|---|---|---|
| 3,480,010 A | 11/1969 | Crossley | |
| 3,805,769 A | 4/1974 | Sessions | |
| 3,911,906 A | 10/1975 | Reinhold, Jr. | |
| 3,989,051 A | 11/1976 | Nozhnikov et al. | |
| 4,140,133 A | 2/1979 | Kastrubin et al. | |
| 4,244,373 A | 1/1981 | Nachman | |
| 4,489,440 A | 12/1984 | Chaoui | |
| RE31,866 E | 4/1985 | Lines et al. | |
| 4,509,521 A | 4/1985 | Barry | |
| 4,519,400 A | 5/1985 | Brenman et al. | |
| 4,527,037 A | 7/1985 | Johnson et al. | |
| 4,690,145 A | 9/1987 | King-Smith et al. | |
| 4,715,367 A | 12/1987 | Crossley | |
| 4,719,922 A | 1/1988 | Padjen et al. | |
| 4,763,656 A | 8/1988 | Nauman | |
| 4,777,954 A | 10/1988 | Keusch et al. | |
| 4,786,277 A | 11/1988 | Powers et al. | |
| 4,867,164 A | 9/1989 | Zabara | |
| 4,895,154 A * | 1/1990 | Bartelt et al. | 607/50 |
| 4,907,602 A | 3/1990 | Sanders | |
| 4,926,878 A | 5/1990 | Snedeker | |
| 5,107,835 A | 4/1992 | Thomas | |
| 5,269,303 A | 12/1993 | Wernicke et al. | |
| 5,397,338 A | 3/1995 | Grey et al. | |
| 5,406,945 A | 4/1995 | Riazzi et al. | |
| 5,511,548 A | 4/1996 | Riazzi et al. | |
| 5,848,966 A | 12/1998 | Gusakov et al. | |
| 5,921,925 A | 7/1999 | Cartmell et al. | |
| 6,023,631 A | 2/2000 | Cartmell et al. | |
| 6,064,901 A | 5/2000 | Cartmell et al. | |
| 6,076,002 A | 6/2000 | Cartmell et al. | |
| 6,129,666 A | 10/2000 | DeLuca et al. | |
| 6,134,480 A | 10/2000 | Minogue | |
| 6,141,575 A * | 10/2000 | Price | 600/372 |
| 6,480,731 B1 | 11/2002 | DeLuca et al. | |
| 6,745,082 B1 * | 6/2004 | Axelgaard | 607/142 |

OTHER PUBLICATIONS

Ira Sanders, M.D., Jonathan Aviv, M.D., Hugh F. Biller, M.D.; *Transcutaneous Electrical Stimulation of the Recurrent Laryngeal Nerve: A Method of Controlling Vocal Cord Position*; Otolaryngology—Head and Neck Surgery, Sep. 1986; pp. 152-157; vol. 95.

Jonathan Aviv, M.D., Michael M. Racenstein, Ira Sanders, M.D., Warren M. Kraus, Hugh F. Biller, M.D.; *Transcutaneous Electrical Stimulation of the Recurrent Laryngeal Nerve in Monkeys*; 1987; pp. 38-42; vol. 96; New York.

Laszlo A. Ilyes, Bsbme, David W. Stepnick, M.D., Michael Broniatowski, Gordon Jacobs, Yukihiko Nose, M.D. Ph.D., Harvey M. Tucker, M.D.; *Artificial Reflux Arc A Potential Solution for Chronic Aspiration, Neck Skin Stimulation Triggering Strap Muscle Contraction in the Canine*; 1987; pp. 331-333; vol. 97; Cleveland, Ohio.

Michael Broniatowski, Charles R. Davies, Jerald C. Kasick, Gordon B. Jacobs, Harvey M. Tucker, Yukihiko Nose; *New Horizons in Dynamic Rehabilitation of Paralyzed Laryngeal Functions*; 1988; pp. 674-680, vol. XXXIV.

Jonathan E. Aviv, M.D., Ira Sanders, M.D., David Silva, M.D., Warren M. Kraus, Bei-Lian Wu, M.D., Hugh F. Biller, M.D.; *Overcoming Laryngospasm by Electrical Stimulation of the Posterior Cricoartyenoid Muscle*; 1989; pp. 110-118; vol. 100, No. 2; New York.

Ira Sanders, M.D.; *Electrical Stimulation of Laryngeal Muscle*; 1991; pp. 1253-1274; vol. 24, No. 5; Otolaryngologic Clinics of North America; New York.

Michael Broniatowski, M.D.; *Dynamic Control of the Larynx and Future Perspectives in the Management of Deglutitive Aspiration*; Dysphagia, 1993, pp. 334-336; vol. 8, Springer-Verlag; New York.

Jaroy Weber, Jr., M.D., Richard A. Jobe, M.D., Robert A. Chase, M.D.; *Evaluation of Muscle Stimulation in the Rehabilitation of Patients With Hypernasal Speech*; Plastic and Reconstructive Surgery, 1970, pp. 173-174, vol. 46, No. 2; The Williams & Wilkins Co.; Stanford, CA.

J. H. Quinn; T. E. Daniels, *The Clinical Effects of Electrostimulation of Salivary Function of Sjogren's Syndrome Patients*, Rheumatology, 1992, pp. 45-45; Springer-Verlag.

George E. Larsen, Ph.D.; *Conservative Management for Incomplete Dysphagia Paralytica*; 1973, pp. 180-185, vol. 54, Arch. Phys. Med. Rehabil.; Seattle, WA.

Nicholas E. Diamanti; *Firing Up the Swallowing Mechanism*, Nature Medicine, 1996; 110-1192, vol. 2, No. 11; Toronto, Canada.

Robert M. Miller, Ph.D.; Michael Groher, Ph.D.; *Speech Language Pathology and Dysphagia: A Brief Historical Perspective*; Dysphagia; 1993, pp. 180-184; Springer-Verlag; New York.

Hiroshi Miki, Wataru Hida, Tatsuya Chonan, Yoshihiro Kikuchi, Tamotsu Takishima; *Effects of Submental Electrical Stimulation During Sleep on Upper Airway Patency in Patients With Obstructive Sleep Apnea*; America Review of Respiratory Disease, 1989; pp. 1285-1289; vol. 140, No. 5; American Thoracic Society.

Q. Aziz, J. C. Rothwell, J. Barlow, A. Hobson, S. Alani, J. Bancewicz, D.G. Thompson; *Esophageal Myoelectric Responses to Magnetic Stimulation of the Human Cortex and the Extracranial Vagus Nerve*; 1994; G827-G-835, The American Physiological Society.

Chi-Fishman, G, Capra NF; McCall GN; *Thermomechanical Facilitation of Swallowing Evoked by Electrical Nerve Stimulation in Cats*; Abstract from Dysphagia; 1994; 1 page; Pubmed Medline Query.

* cited by examiner

METHOD AND APPARATUS FOR TREATING OROPHARYNGEAL DISORDERS WITH ELECTRICAL STIMULATION

RELATED APPLICATIONS

This application is a continuation-in part of U.S. application Ser. No. 10/308,105, filed Dec. 3, 2002 now abandoned and entitled "Method And Apparatus For Treating Oropharyngeal, Respiratory And Oral Motor Neuromuscular Disorders With Electrical Stimulation", which is a continuation of U.S. application Ser. No. 09/757,804, filed Jan. 11, 2001 now abandoned, which is a continuation of U.S. application Ser. No. 09/236,829, filed Jan. 25, 1999 (now U.S. Pat. No. 6,148,970), which is a continuation-in-part of U.S. application Ser. No. 08/956,448, filed Oct. 23, 1997 (now U.S. Pat. No. 5,987,351), which is a continuation of U.S. application Ser. No. 08/549,046, filed Oct. 27, 1995 (now U.S. Pat. No. 5,725,564).

FIELD OF THE INVENTION

This invention relates to a method and apparatus for effectively treating oropharyngeal disorders. In particular, the present invention relates to a method and apparatus for treating oropharyngeal disorders by providing electrical stimulation to specific areas of a patient's throat using one or more pairs of snap electrodes.

BACKGROUND OF THE INVENTION

Asymptomatic and symptomatic oropharyngeal disorders can lead to an inability to swallow or difficulty in swallowing. These disorders may be caused, for example, by stroke. neurodegenerative diseases, brain tumors or respiratory disorders.

Swallowing is a complicated action whereby food is moved from the mouth through the pharynx and esophagus to the stomach. The act of swallowing may be initiated voluntarily or reflexively but is always completed reflexively.

The act of swallowing occurs in three stages and requires the integrated action of the respiratory center and motor functions of multiple cranial nerves, and the coordination of the autonomic system within the esophagus. In the first stage, food or some other substance is placed on the surface of the tongue. The tip of the tongue is placed against the hard palate. Elevation of the larynx and backward movement of the tongue forces the food through the isthmus of the fauces in the pharynx. In the second stage, the food passes through the pharynx. This involves constriction of the walls of the pharynx, backward bending of the epiglottis, and an upward and forward movement of the larynx and trachea. Food is kept from entering the nasal cavity by elevation of the soft palate and from entering the larynx by closure of the glottis and backward inclination of the epiglottis. During this stage, respiratory movements are inhibited by reflex. In the third stage, food moves down the esophagus and into the stomach. This movement is accomplished by momentum from the second stage, peristaltic contractions, and gravity.

Although the main function of swallowing is the propulsion of food from the mouth into the stomach, swallowing also serves as a protective reflex for the upper respiratory tract by removing particles trapped in the nasopharynx and oropharynx, returning materials to the stomach that are refluxed into the pharynx, or removing particles propelled from the upper respiratory tract into the pharynx. Therefore, the absence of adequate swallowing reflex greatly increases the chance of pulmonary aspiration.

In the past, patients suffering from oropharyngeal disorders have undergone dietary changes or thermal stimulation treatment to regain adequate swallowing reflexes. Thermal stimulation involves immersing a mirror or probe in ice or another cold substance. The tonsillar fossa is stimulated with the mirror or probe, and the patient closes his mouth and attempts to swallow. While these traditional methods are usually effective for treating oropharyngeal disorders, in some patients these methods require that the patient endure weeks or months of therapy. It is also difficult to distinguish patients who require such treatments from patients who recover spontaneously. Thus, it is desirable to have a simple, non-invasive method and device for treating oropharyngeal disorders and artificially promoting swallowing which is effective within a relatively short treatment period.

Electrical stimulation has been used as a method for alleviating pain and stimulating nerves, as well as a means for treating disorders of the spinal cord or peripheral nervous system. Electrical stimulation has further been used to facilitate muscle reeducation and with other physical therapy treatments. In the past, electrical stimulation was not recommended for use in the neck because of concerns that the patient would develop spasms of the laryngeal muscles, resulting in closure of the airway or difficulty in breathing, and/or because of concerns that the introduction of electrical current into the neck near the carotid body would cause cardiac arrhythmia.

More recently, electrical stimulation has been used to stimulate the recurrent laryngeal nerve to stimulate the laryngeal muscles to control the opening of the vocal cords to overcome vocal cord paralysis, to assist with the assessment of vocal cord function, to aid with intubation, and other related uses. Generally, there have been no adverse reactions to such treatment techniques. However, electrical stimulation has not been used in the treatment of oropharyngeal disorders to promote the swallowing reflex, which involves the integrated action of the respiratory center and motor functions of multiple cranial nerves.

SUMMARY OF THE INVENTION

The present invention provides a simple, non-invasive method and apparatus for treating oropharyngeal disorders and artificially promoting swallowing by providing electrical stimulus to the pharyngeal region of a patient (a human or other animal).

The method and apparatus for electrical pharyngeal neuromuscular stimulation according to the present invention are more effective for treating oropharyngeal disorders than traditional treatment methods, such as thermal stimulation. Further, the method and apparatus of the present invention are effective for treating worst-case dysphagia resulting from neurodegeneration and strokes.

An apparatus for treating oropharyngeal disorders according to the present invention includes a first electrode and a second electrode. Each of these electrodes includes a snap eyelet, a conductive film and an adhesive and conductive gel layer. The snap eyelet has a first side and a second side, and the second side has a connector to which a lead wire may be attached. The conductive film is attached to the first side of the snap eyelet, and the adhesive and conductive gel layer is attached to the conductive film and adapted to be attached to the skin of the patient. The apparatus also includes at least one adhesively backed tape overlay for securing the first and second electrodes to the skin of the patient. Further, the apparatus includes a pulse generator for generating a series of electrical pulses. The pulse generator includes a frequency controller, a duration control circuit and an intensity control circuit. The frequency controller is adapted for modulating an electrical signal generated by the pulse generator at a predetermined frequency to produce the series of electrical pulses. The duration control circuit is adapted for controlling the duration of time for which said pulse generator generates the series of electrical pulses, and the intensity control circuit is adapted for regulating the series of electrical pulses such that the electrical current does not exceed a predetermined current or voltage value. The pulse generator also includes an output jack for connection of a lead wire. The apparatus also includes at least one lead wire having an electrode connection end and an output jack end. The electrode connection end is adapted to be attached to a connector of a snap eyelet, and the output jack end is adapted to be attached to the output jack of the pulse generator.

The method of the invention includes providing the apparatus described above. In addition, according to the method, the first and second electrodes are placed on the skin of the patient's throat with the adhesive gel layer in contact with the skin, and the electrodes are secured to the skin of the patient's throat by application of at least one adhesively backed tape overlay to the patient's skin over at least a portion of each of the electrodes. A lead wire is attached to the snap eyelet of each electrode and to the output jack of the pulse generator, and a series of electrical pulses is generated using the pulse generator so as to apply the series of electrical pulses to the patient's throat using the electrodes.

In a preferred embodiment of the invention, a novel electrode may be utilized in a novel arrangement to effect stimulation of the muscles and nerves in the oropharyngeal region of the patient's throat. Each such preferred electrode comprises a snap eyelet having a first side and a second side. The first side of each snap eyelet is generally circular and has a diameter of about 7 mm. The second side has a stud connector to which a lead wire may be attached. The preferred electrode also includes a generally circular conductive film having a diameter within the range of 16 mm–22 mm that is attached to the first side of the snap eyelet. The preferred electrode also includes an adhesive and conductive layer of cross-linked hydrogel that is attached to the conductive film and adapted to be attached to the skin of the patient. Each such preferred snap electrode provides a halo or circle of electrical output, such that the electrical field is concentrated at the outer circumference of the electrode and not evenly dispersed over the surface of the electrode. This is in contrast to pin-type electrodes, commonly used in electrical stimulation applications, which provide an even, dispersed field of electrical output over the entire surface of the electrode. As a result of the concentration of the electrical output of snap electrodes around their circumferences, less electrical intensity is required to treat the patient when using snap electrodes than when using pin electrodes. Thus, the electrical output produced by the novel size and arrangement of snap electrodes according to the present invention enables the stimulated muscles to achieve stronger squeeze and contractility without exceeding the tolerance or comfort level of the patient. In contrast, achieving the same degree of squeeze and contractility with larger, standard electrodes requires the use of a substantially higher intensity of electrical stimulation, which frequently exceeds the tolerance or comfort level of the patient and may cause the adverse effect of spasm of the laryngeal muscles. Moreover, the size of the conductive film of the preferred snap electrode is reduced from the size commonly used for therapeutic application, providing for additional treatment flexibility.

These and other aspects of the invention will be apparent to those skilled in the art to which the invention relates upon reading and understanding the specification that follows:

DETAILED DESCRIPTION OF THE PREFERRED EMBODIMENTS

Figure 1:
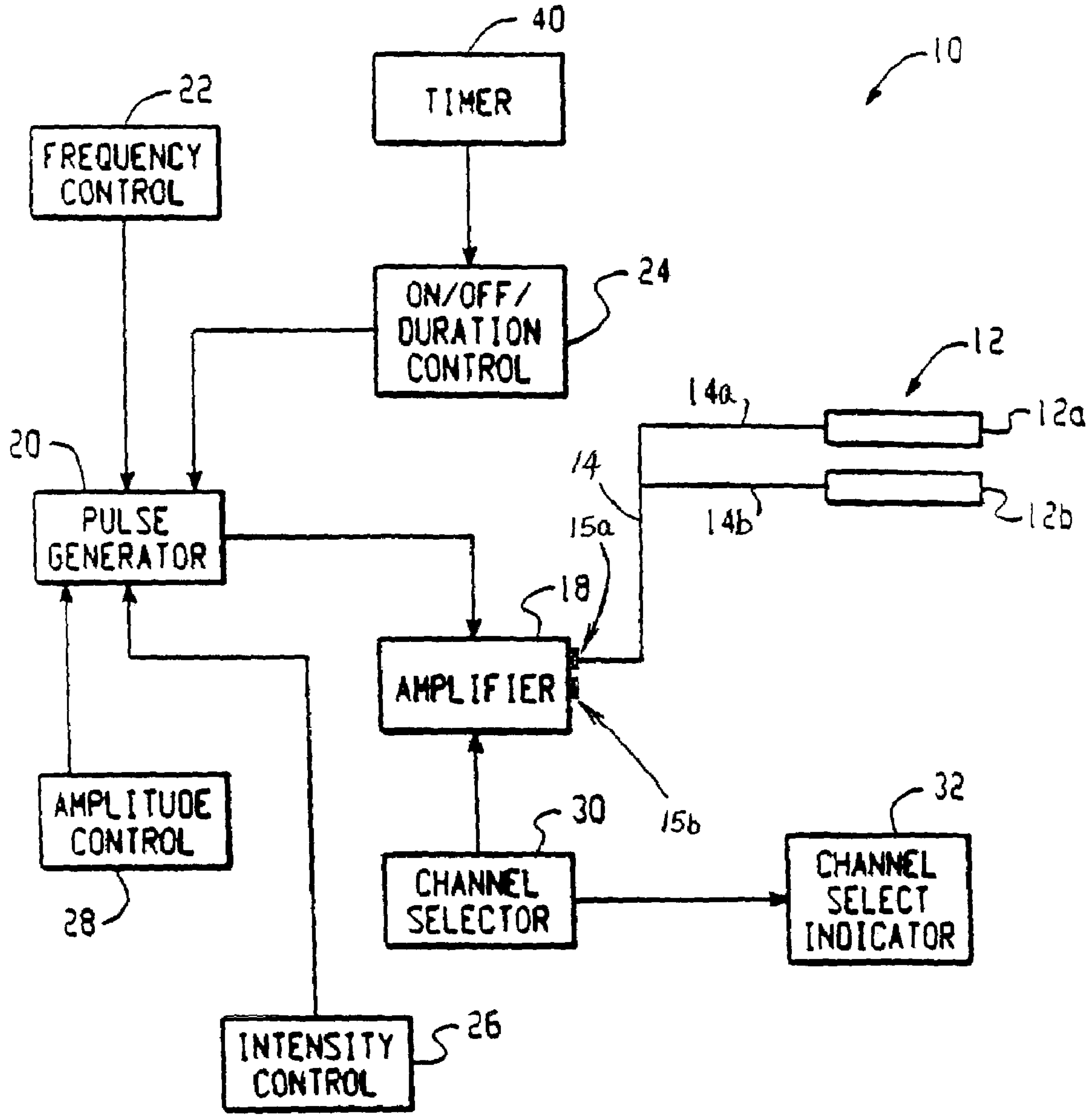
FIG. 1 is a diagram of an electrical neuromuscular stimulator according to the present invention for use in treating dysphagia and other oropharyngeal disorders.

The present invention will now be described in detail with reference to the accompanying drawings, which are provided as illustrative examples of embodiments of the invention only and not for purposes of limiting the same. In the drawings, like reference numerals indicate like elements throughout the several views.

FIG. 1 illustrates a preferred embodiment of an electrical neuromuscular stimulation device 10 for providing electrical neuromuscular stimulus to the oropharyngeal region of a patient in order to artificially promote swallowing. The electrical neuromuscular stimulation device 10 as shown in FIG. 1 is comprised of electrodes 12 (including individual electrodes 12*a* and 12*b*) that are adapted to be selectively placed in electrical contact with tissue of a patient, and a pulse generator 20 for generating a series of electrical pulses, which is coupled to each of the electrodes 12*a* and 12*b*.

Figure 10:
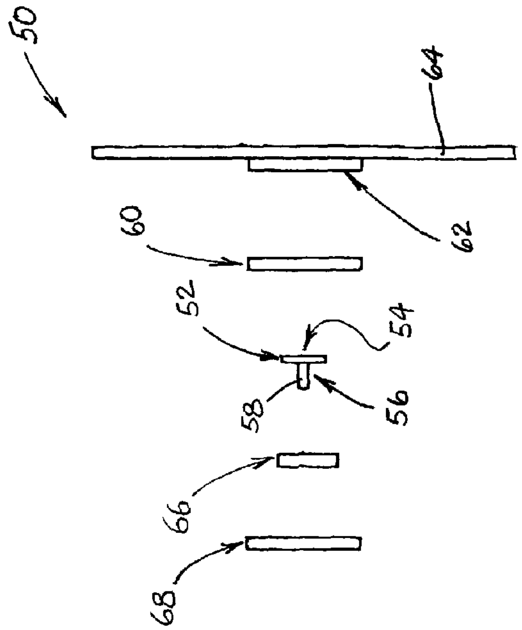
FIG. 10 is an exploded view of a preferred embodiment of an electrode of the invention.

The device 10 preferably includes at least two electrodes 12*a* and 12*b*, although four electrodes (not shown in FIG. 1) may also be employed in connection with the invention. For human applications, the electrodes 12 are preferably snap electrodes having a construction such as is illustrated in FIG. 10 (described in more detail hereinafter).

At least one lead wire, such as lead wire 14, is provided as a part of the apparatus. Each such lead wire has an electrode connection end for connection to an electrode and an output jack end for connection to the pulse generator. These connection ends may be of conventional design or any design that is suitable for connecting an electrode to an output jack of the pulse generator, as would be appreciated by those having ordinary skill in the art to which the invention relates. In a preferred embodiment, lead wire 14 has a pair of electrode connection ends 14*a* and 14*b* which are attached to electrodes 12*a* and 12*b* respectively, and an output jack end that is attached to output jack 15*a* of amplifier 18 of pulse generator 20. In the preferred embodiment illustrated in FIG. 1, a second output jack 15*b* is also provided. Lead wire 14 may be made from any physiologically acceptable conductive metal, preferably insulated aluminum or copper wire. Multistrand wire is preferable to "wire wrap" wire because multistrand wire is softer and less likely to break with repeated flexing.

The series of electrical pulses is generated by selective control of pulse generator 20, which provides the series of electrical pulses to the plurality of electrodes 12 via amplifier 18. Pulse generator 20 preferably includes a frequency controller 22 (shown as separate component in FIG. 1) which modulates an electrical signal generated by the pulse generator at a predetermined frequency to produce the series of electrical pulses output by the pulse generator 20. The frequency controller 22 may modulate the electrical signal at a fixed frequency, for example, 80 hertz, or may vary the frequency of the electrical pulses within a predetermined range of frequencies, for example, a range of frequencies from 4 to 80 hertz. Other frequency ranges as are known to those having ordinary skill in the art to which the invention relates may also be used. Generally, the frequency of the electrical pulses is selected in order to provide the greatest comfort to the patient and to minimize as much as possible the amount of pin-prick sensation felt by the patient.

The pulse generator 20 also preferably includes a duration control 24 for controlling the duration of time for which pulse generator 20 outputs the series of electrical pulses. The duration control 24 may control pulse generator 20 to output the electrical pulses for a fixed duration, for example, generally fixed at 300 microseconds. Alternatively, the duration control 24 may control pulse generator 20 to output the electrical pulses for varying durations within a predetermined range, for example a range of 50 to 300 microseconds, and may further create one or more pauses of varying duration during the application of the electrical pulses to the patient's tissue. Other durations as are known to those having ordinary skill in the art to which the invention relates may also be used. The duration control 24 may be adjusted manually or automatically using conventional circuits, such as a timer 40.

In the embodiment depicted in FIG. 1, the pulse generator also includes an intensity control circuit 26 (shown as a separate component in FIG. 1) for regulating the series electrical pulses such that the electrical current does not exceed a predetermined current value, for example, 25 milliamps RMS, and the power does not exceed a predetermined voltage value, for example, 9.6 milliwatts RMS, or both. In a preferred embodiment, the intensity control circuit 26 limits the current and voltage values of the electrical pulses output by pulse generator 20 using conventional limiter circuits. The predetermined current and voltage values may vary in accordance with the patient's physical condition and tolerances and the treatments performed. Generally, the intensity of the current and voltage outputs is determined in order to provide the greatest comfort to the patient and to minimize as much as possible the amount of pin-prick sensation felt by the patient.

For example, in treatment of oropharyngeal disorders, the current applied should be sufficient to produce the desired response and promote the swallowing reflex. The intensity of the current is increased by small increments until the swallow response or muscle fasciculation occurs. However, the current that is applied should not be too intense in order to avoid laryngeal spasms or cardiac arrhythmia in the patient.

In the preferred embodiment depicted in FIG. 1, pulse generator 20 also includes an amplitude control circuit 28 (shown as a separate component in FIG. 1). Amplitude control circuit 28 allows for selective control of the amplitude of the electrical pulses generated by pulse generator 20 by manually or automatically operated conventional circuits as are known to those having ordinary skill in the art to which the invention relates.

In a preferred embodiment, channel selector 30 suitably forms another input to amplifier to allow for concurrent activation of additional electrode pairs (not shown in FIG. 1) using conventional switching circuits through different output jacks, such as output jack 15*a* (to which lead wire 14 is attached) and output jack 15*b*. In such embodiment, intensity control circuit 26 may be employed to independently regulate the current of a series of electrical pulses that are output through the pair of output jacks. Preferably, the current of the pulses output through output jack 15*a* may be regulated within the range of 0.5 to 25 milliamps in 0.5 milliamp increments. Similarly and independently, the current of the pulses output through output jack 15*b* may be regulated within the range of 0.5 to 25 milliamps in 0.5 milliamp increments. The status of channel selector 30 is indicated by a channel selector indicator 32.

In one embodiment of the present invention, the pulse generator 20 continuously generates electrical pulses for a predetermined period of time. For example, electric pulses may be continuously generated and delivered to the electrodes until a complete swallow is achieved or the sensory tolerance level is reached in the patient. Additional treatments wherein the generator continuously generates electric pulses are suitably performed on the patient as necessary. In an alternative embodiment of the present invention, the pulse generator 20 selectively generates cycles of electrical pulses. In this embodiment, pulse generator 20 includes a treatment time control function, which is accomplished with intensity control 26 in response to real time information provided by timer 40. The timer 40, intensity control 26, and pulse generator 16 also serve to provide functions of treatment time control, on-ramp control, and off-ramp control.

In a preferred embodiment, the treatment time control function selectively controls the duration of time wherein the pulse generator 20 selectively generates cycles of electric pulses. The treatment time is any suitable period, such as fifteen, thirty, or sixty minutes, or the treatment time control function may allow for manually controlled continuous treatment. As with all settings, the particular values are highly specific to the application and patient. Thus, a suitable duration of the electric pulses in each cycle is manually or automatically set. In one embodiment according to the present invention, the duration of electric pulses in each cycle is within the range of 0.5 seconds to 30 seconds. Other durations as are known to those having ordinary skill in the art to which the invention relates may also be used.

In a preferred embodiment, the treatment time control function also selectively controls the amount of time between each treatment cycle. For example, the treatment time control may be set to provide a delay between treatment cycles of about ranging from 0.1 seconds to 60 seconds. Other ranges as are known to those having ordinary skill in the art to which the invention relates may also be used.

In a preferred embodiment, the on-ramp control function controls the amount of time required to reach the maximum intensity in each cycle. In one embodiment of the present invention, the amount of time required to reach the maximum intensity is between approximately 0.1 and 6.0 seconds. Other times as are known to those having ordinary skill in the art to which the invention relates may also be used.

In a preferred embodiment, the off-ramp control function controls the amount of time required to decrease from the maximum intensity to zero intensity at the end of each cycle. In one embodiment of the present invention, the amount of time required to decrease from the maximum intensity to zero intensity is between approximately 0.1 and 6.0 seconds. Other times as are known to those having ordinary skill in the art to which the invention relates may also be used. A suitable commercially available device that provides the functions described above is the VitalStim device manufactured by the Chattanooga Group Division of Encore Medical LP, which division is located in Chattanooga, Tenn.

An alternative embodiment of a device for electrical neuromuscular stimulation according to the present invention will now be described with reference to FIG. 6. Shown therein is a microprocessor-based stimulation device 600 according to the present invention including a microprocessor 601, a bi-directional analog switching network 602, and a plurality of pulse generators 603, 604, 605 and 606. Microprocessor 601 controls the operation of pulse generators 603 through 606 by generating control signals indicating the parameters for generation of electrical pulses for each pulse generator 603 through 606 respectively. For example, control signals provided by microprocessor 601 to each pulse generator 603 through 606 may include waveform, intensity, pulse width, ramp-on, and ramp-off control signals. Upon receipt of the respective control signals from microprocessor 601, pulse generators 603 through 606 generate electrical pulses and output the pulses to bi-directional analog switching network 602.

Figure 6:
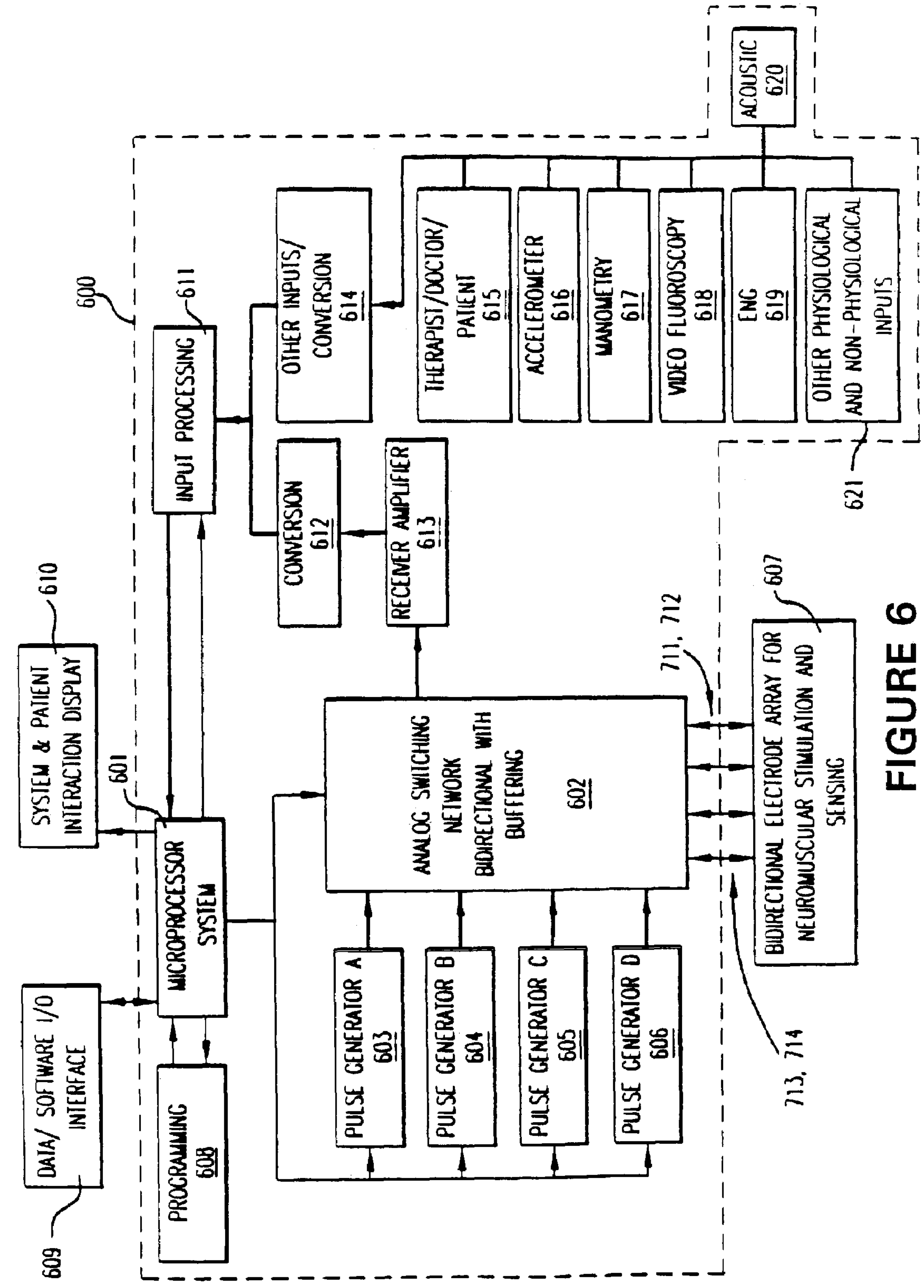
FIG. 6 is a block diagram of an alternative embodiment of an electrical neuromuscular stimulator according to the present invention, including a microprocessor system, a plurality of pulse generators, and a bi-directional analog switching network.

In the embodiment depicted in FIG. 6, microprocessor 601 is also coupled to bi-directional analog switching network 602 and provides control signal to switching network 602 to control the operation of switching network 602 in processing and selectively outputting the electrical pulses to a bi-directional electrode array 607 coupled to switching network 602. Switching network 602 receives electrical pulses generated by each of pulse generators 603 through 606. Based upon the control signals from microprocessor 601 to switching network 602, switching network 602 outputs the electrical pulses from one or more of pulse generators 603 through 606 to electrodes 701, 702, 703 and 704 (FIG. 7A) in electrode array 607 via lead wires 710, 711, 712, and 713 respectively. The control signals from microprocessor 601 to switching network 602 determine, for example, the sequence in which the electrical pulses from each of pulse generators 603 through 606 are provided to each electrode in electrode array 607 and the duration for which electrical pulses from each pulse generator will be provided to each electrode. Notably, switching network 602 may include one or more conventional buffer memories (not shown) to prevent overloading of the network.

According to one embodiment of the present invention, microprocessor 601, switching network 602 and pulse generators 603 through 606 may be designed to provide maximum flexibility of operation. Thus, each of the pulse generators may be capable of providing electrical pulses having either fixed or variable current and voltage values, modulation rates and frequencies. The waveform, intensity, and ramp-on and ramp-off functions provided by each pulse generator 603 through 606 may also be variably selected. Stimulation device 600 allows each of pulse generators 603 through 606 to independently produce simultaneous and/or sequential stimulation by each of the electrodes in electrode array 607. Generally, the waveform and intensity of the electrical pulses is selected and/or pre-programmed in order to provide the greatest comfort to the patient and to minimize as much as possible the amount of pin-prick sensation felt by the patient.

In the preferred embodiment depicted in FIG. 6, microprocessor 601 is coupled to a programming device 608, which enables the microprocessor to be programmed to perform the processing functions in accordance with the present invention. Data may also be provided to microprocessor 601 by programming device 608. Programming of microprocessor 601 and downloading of data to the microprocessor may be accomplished through a conventional interface, such as standard RS232 serial and parallel ports or infrared links, as is known to those having ordinary skill in the art to which the invention relates.

Stimulation device 600 depicted in FIG. 6 also includes a feedback network for receiving and processing feedback received from electrode array 607. For example, electrode array 607 may use electromyographic (EMG) sensing capabilities to generate electrical feedback signals. The EMG sensing capabilities are utilized, for example, to determine whether muscles are contracting and, if so, the sequence of muscle contractions. This information may be used to adjust the electrical pulses supplied to stimulate these muscles. In treatments of oropharyngeal disorders, muscle contraction information may also be used to identify the patient's attempts to swallow, enabling the stimulator to facilitate the remainder of the swallowing sequence.

The feedback signals generated by electrode array 607 are provided to switching network 602 that outputs the feedback signals to a receiver amplifier 613. Receiver amplifier 613 amplifies the feedback signals and outputs the amplified feedback signals to a conversion circuit 612. Conversion circuit 612 formats the amplified feedback signals into a selected signal format and outputs the formatted feedback signals to an input processor 611. The selected signal format into which conversion circuit 612 converts the feedback signals is selected to enable input processor 611 to download and process the feedback signals.

In the preferred embodiment depicted in FIG. 6, input processor 611 also optionally receives one or more physiological and/or non-physiological inputs from input devices 615, 616, 617, 618, 619, 620 and 621. The physiological input devices such as devices 616, 617, 618, 619 and 620 provide inputs representing various physiological characteristics of the patient. For example, physiological inputs may be received from such devices as an accelerometer 616 (indicating motion due to a contraction of the muscle during swallowing), a manometry device 617 (indicating pressure increase due to the attempt at swallowing). a video fluoroscopy device 618 (for providing an input from visual examination of the patient's swallowing mechanism to determine the effectiveness of the swallow), an EMG device 619 (indicating muscle movements in the oral motor muscles and/or swallowing mechanism which may not be detected by the electrode stimulation patch), and/or an acoustic signaling device 620, e.g., a microphone placed on the neck of the patient, to detect speech and/or swallowing sounds.

Non-physiological devices such as device 615 may provide inputs representing various non-physiological characteristics of the patient. Non-physiological inputs may be received from such sources as therapist/patient/doctor input device 615 which enables a therapist, patient and/or doctor to enter information such as the patient's threshold for the stimulation device parameters, including a minimum threshold needed and the maximum intensity usable for the patient, as well as parameters for altering the sequence and intensity of electrode stimulation for the patient based upon asymmetries which the patient may have during the swallowing process, respiratory process or oral motor stimulation process.

Additional factors such as height, weight, neck thickness/size, torso measurements, facial dimensions, pain tolerance, and the current status of the patient's ability to swallow may be entered for use in determining the appropriate stimulation frequency patterns and intensities. Additional physiological and/or non-physiological inputs may be received from other devices as indicated by representative input device 621.

In a preferred embodiment, the physiological and non-physiological inputs respectively generated by physiological and non-physiological input devices 615 through 620 are formatted by a conversion circuit 614 (similar to conversion circuit 612) and then stored and processed by input processor 611. Input processor 611 processes and stores as test data both the feedback signals originated by electrode array 607 and physiological and non-physiological inputs from devices 615 through 620. Input processor also receives control signals and data inputs from microprocessor 601.

In the preferred embodiment depicted in FIG. 6, a system and patient interaction display 610 is optionally provided. Display 610 is coupled to microprocessor 601 and receives processed data from input processor 611 via microprocessor 601. In this manner, display 610 enables monitoring of the feedback signals from electrode array 607 in addition to the status of inputs from the various physiological and non-physiological inputs 615 through 620 as described above. Display 610 may also enable monitoring of the operating status of stimulation device 600.

The display 610 may display a variety of parameters, inputs, and outputs as may be desired. For example, display 610 may show current patient parameters, current inputs from the physiological and non-physiological devices and the electrode stimulation array, an overall rating of swallowing capability and current swallowing effectiveness, and the current setting(s) of the stimulation pattern frequency and/or intensity. Additionally, the display 610 may be adapted for monitoring by the patient to provide feedback to the patient as to how well swallowing has been completed. This feedback to the patient may assist with the patient's inherent bio-feedback mechanisms.

In the preferred embodiment depicted in FIG. 6, a data/software I/O interface 609 is optionally provided to enable downloading of testing data collected and processed by stimulation device 600, for example, during patient treatments. Patient-specific data may be downloaded to external devices, including portable devices, through any conventional interface (e.g., a hardwired interface, coaxial interface, infrared interface, etc.).

Referring now to FIG. 10, preferred electrode 50 is illustrated, comprising a metal snap eyelet 52 having a first side 54 and a second side 56. The first side of each preferred snap eyelet is generally circular and has a diameter of about 7 mm. The second side has a stud connector 58 to which a lead wire may be attached. The preferred electrode also includes a generally circular conductive film 60 having a diameter within the range of 16 mm–22 mm that is attached to the first side of the snap eyelet. Preferably, conductive films at the lower end of this size range, or dime-sized films, are used in electrodes intended for application to children, whereas films at the upper end of the preferred range, or nickel-sized films, are used in electrodes intended for application to adults. As used herein, the term "conductive film" refers to a thin substrate that is electrically conductive. Preferably, the film is a carbon film having a thickness of about 0.10 mm. However, other conductive substrates as are known to those having ordinary skill in the art to which the invention relates may also be employed. The preferred electrode also includes an adhesive and conductive gel layer 62, preferably of cross-linked hydrogel having a thickness of about 1.0 mm, that is attached to the conductive film and adapted to be attached to the skin of the patient. For application of the electrodes to children, hi-tack versions of the adhesive gel layer are preferred because of the relatively small skin-contact area. A hi-tack conductive gel adhesive known as RG-72 is available from the Promeon Company. The preferred electrode also includes a release liner 64 that is attached to the gel layer to protect it prior to application to the skin of the patient. Preferably, the release liner is made of polyester or other suitable material having a thickness of about 0.125 mm. The electrode of the invention may also include a conductive bond tape layer 66, having a hole for the stud, that is adapted to more securely attach eyelet 52 to conductive film 60. An electrically-insulating layer 68 may also be provided to overlie the conductive bond tape layer, or if there is no such layer, the eyelet itself. The insulating layer will also include a hole through which the stud may protrude. Preferred results have been obtained when the maximum electrical impedance of the electrode is about 150 ohms.

Figure 7:
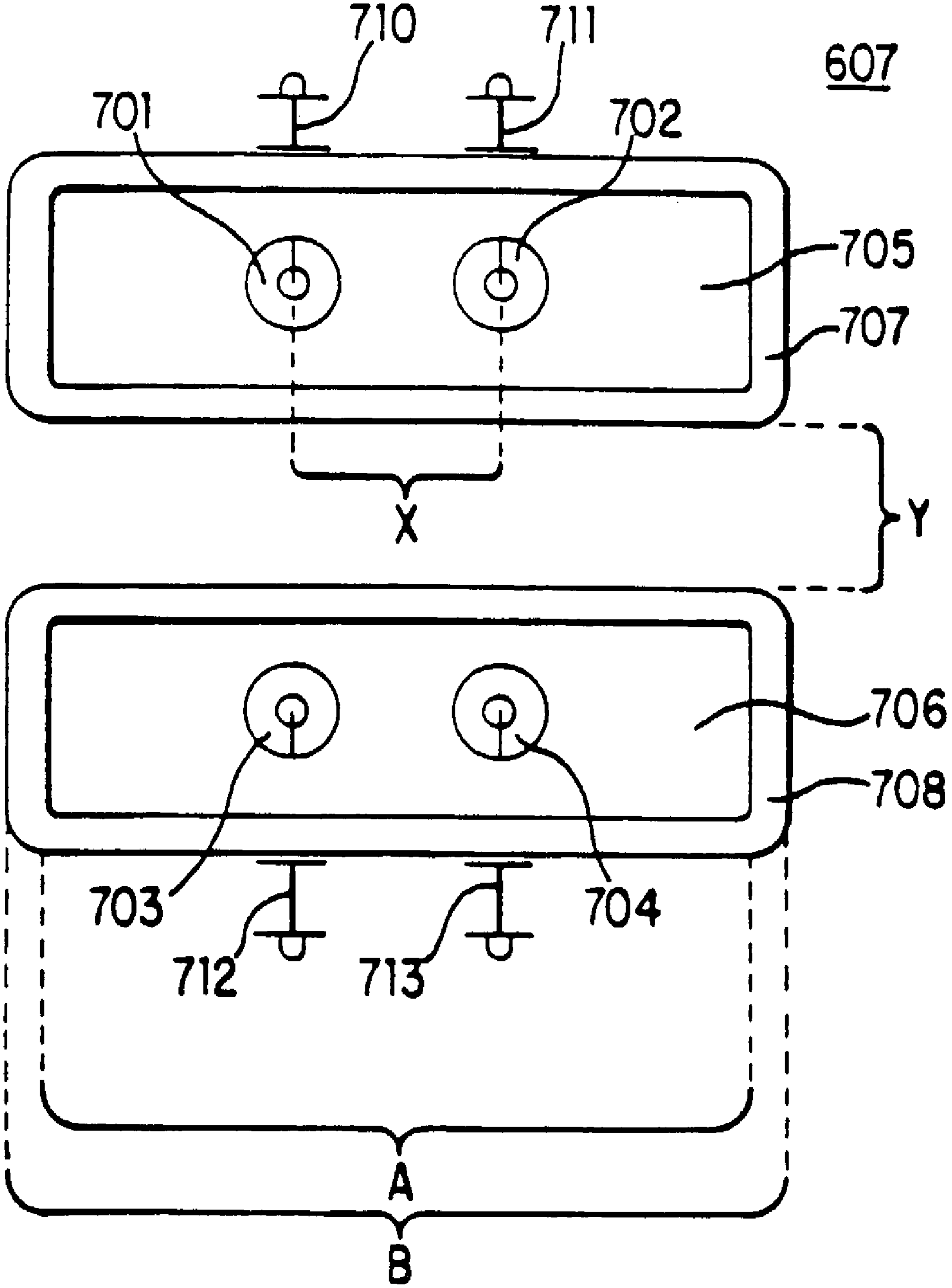
FIG. 7 is a diagram of an electrode array that may be used in conjunction with the embodiment of FIG. 6 to provide neuromuscular stimulation to a patient and to provide feedback signals to the bi-directional analog switching network of FIG. 6.

A preferred embodiment of a bi-directional electrode array 607 for use in conjunction with stimulation device 600 for treatment of oropharyngeal disorders is illustrated in FIG. 7. Each bi-directional electrode in array 607 stimulates one or more pharyngeal muscles with electrical stimulation provided by the switching network 602, detects the electromyographic (EMG) response from the stimulated muscle(s), and provides the EMG response as an electrical feedback signal to the switching network 602.

Notably, the arrangement of electrodes and connecting wires shown in FIG. 7 is provided as an example and is not intended to limit the scope of the present invention. Unidirectional electrodes (stimulating muscles but not sensing EMG signals from the stimulated muscles) may also be used in accordance with the present invention. Also, multiple electrodes, including squares of four, sixteen, twenty-five, or thirty-six electrodes or more, or vertically arranged pairs of two or four electrodes may be used. As the number of electrodes increases, the surface area treated by the array may be increased and/or the electrodes may be more closely positioned.

Figure 7A:
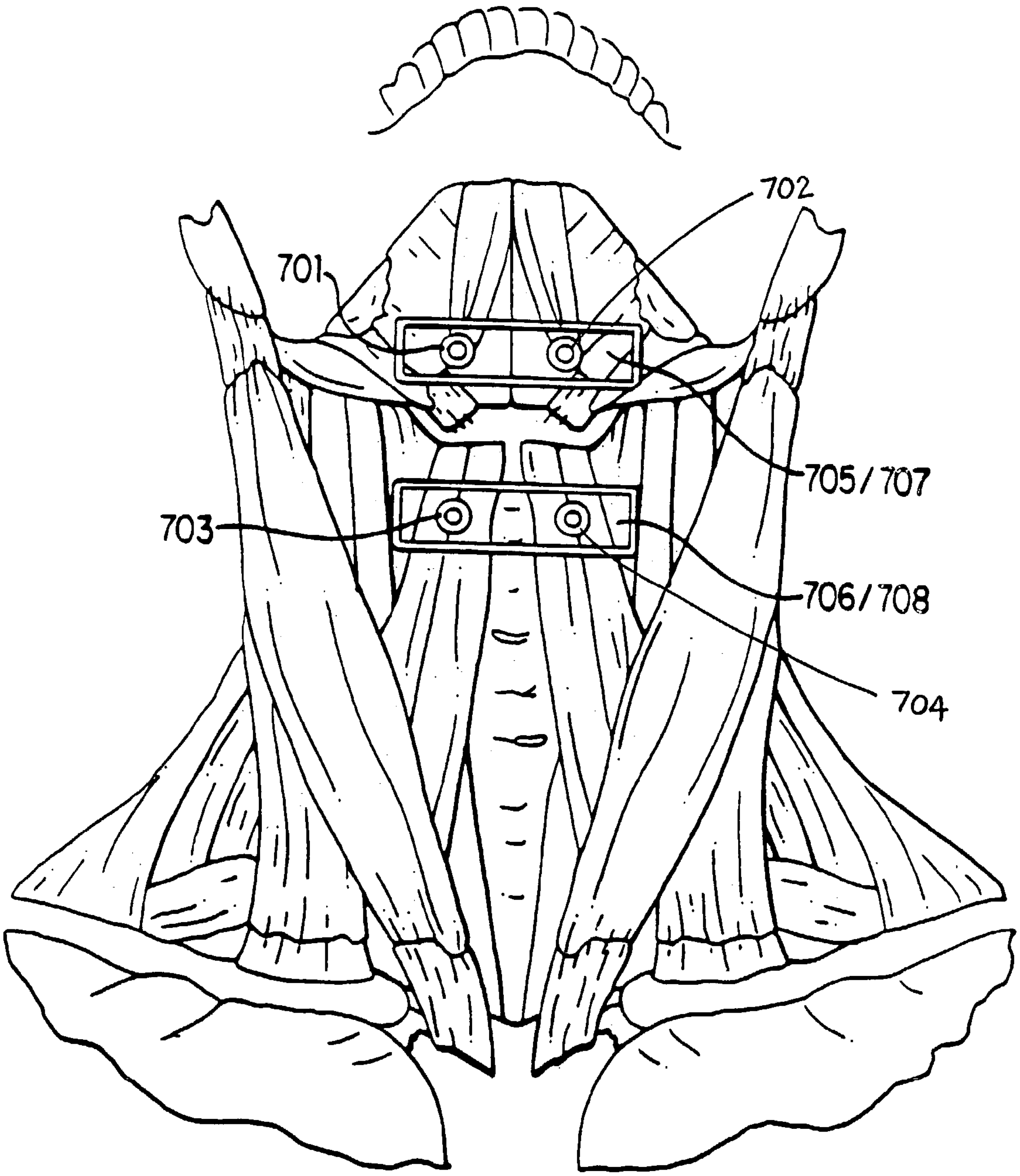
FIG. 7A illustrates the placement of an arrangement of electrodes including four bi-directional electrodes on the pharyngeal region of a human patient.
Figure 9:
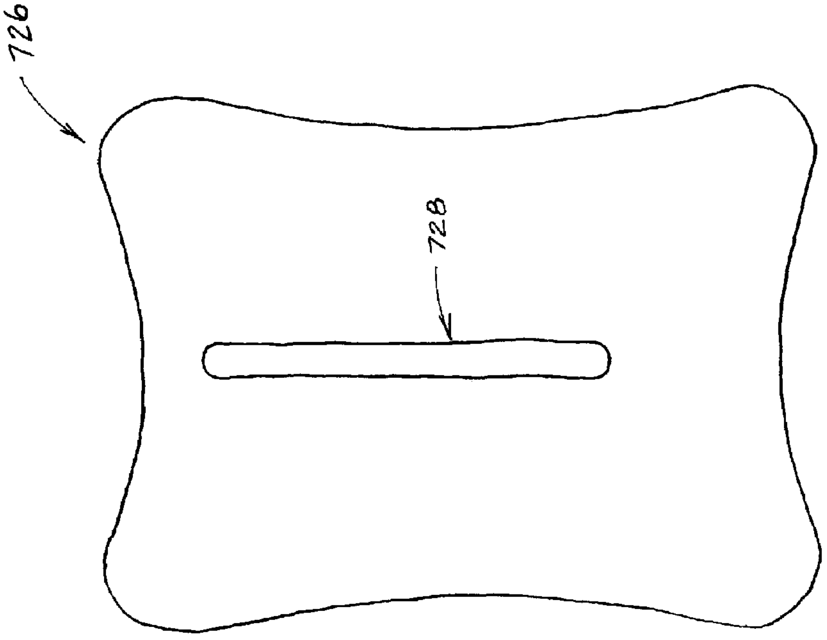
FIG. 9 is a front view of a preferred novel adhesively backed tape overlay for use in securing electrodes to the skin of a patient according to the invention.

As shown in FIG. 7, array 607 preferably comprises four bi-directional electrodes 701, 702, 703 and 704, which are positioned on the tissue of the pharyngeal region of a patient using adhesive bands 705 and 706 as illustrated in FIG. 7A or more preferably, with a pair of adhesively backed tape overlays such as are illustrated in FIG. 9 (and described hereinafter in more detail). The adhesive bands illustrated in FIGS. 7 and 7A for attachment of each pair of electrodes in array 607 to the patient may have a width of approximately eight centimeters, shown as distance "A" in FIG. 7. Contact pads 707 and 708 having a width of approximately eight and a half centimeters (shown as distance "B" in FIG. 7) are also provided.

In the embodiment of the invention illustrated in FIGS. 7 and 7A, the electrodes are preferably arranged in two vertical pairs, each pair on one lateral side (e.g., the right hand or left hand side) of the pharyngeal region of the patient, with one electrode positioned above the patient's Adams Apple and the other below the Adams Apple of the patient. The first pair of electrodes (701, 703) is positioned on the patient's left side (the right side of FIGS. 7 and 7A). The second pair of electrodes (702, 704) is positioned in the same arrangement on the opposite side of the patient's pharyngeal region. Each pair of electrodes may preferably be positioned such that the distance between the centers of the electrodes, shown as distance "X" in FIG. 7, may be approximately three to four centimeters or other spacing as required to position the electrodes on the pharyngeal region of the patient as described above. The pairs of electrodes may preferably be spaced at a distance, shown as distance "Y" in FIG. 7, of approximately two and a half centimeters or other spacing as required to position the electrodes on the pharyngeal region of the patient as described above. In the two-pair electrode arrangement described above, the two electrodes (701, 703) positioned on one lateral side (e.g., right or left side) of the patient's pharyngeal region are coupled to a first output channel of the switching network 602, and the two electrodes (702, 704) positioned on the other lateral side of the patient's pharyngeal region are coupled to a second output channel of the switching network 602.

In the preferred embodiment of FIGS. 7 and 7A, each electrode of electrode array 607 is independently coupled to an output of switching network 602 (shown in FIG. 6) by lead wires 710, 711, 712, and 713 respectively. As a result, each electrode independently receives one or more series of electrical pulses generated by one or more of pulse generators 603–606 via switching network 602 as determined by microprocessor 601. Microprocessor 601 controls the switching operation of switching network 602 to control which output or outputs from pulse generators 603–606 are provided to each electrode in electrode array 607.

Figure 7B:
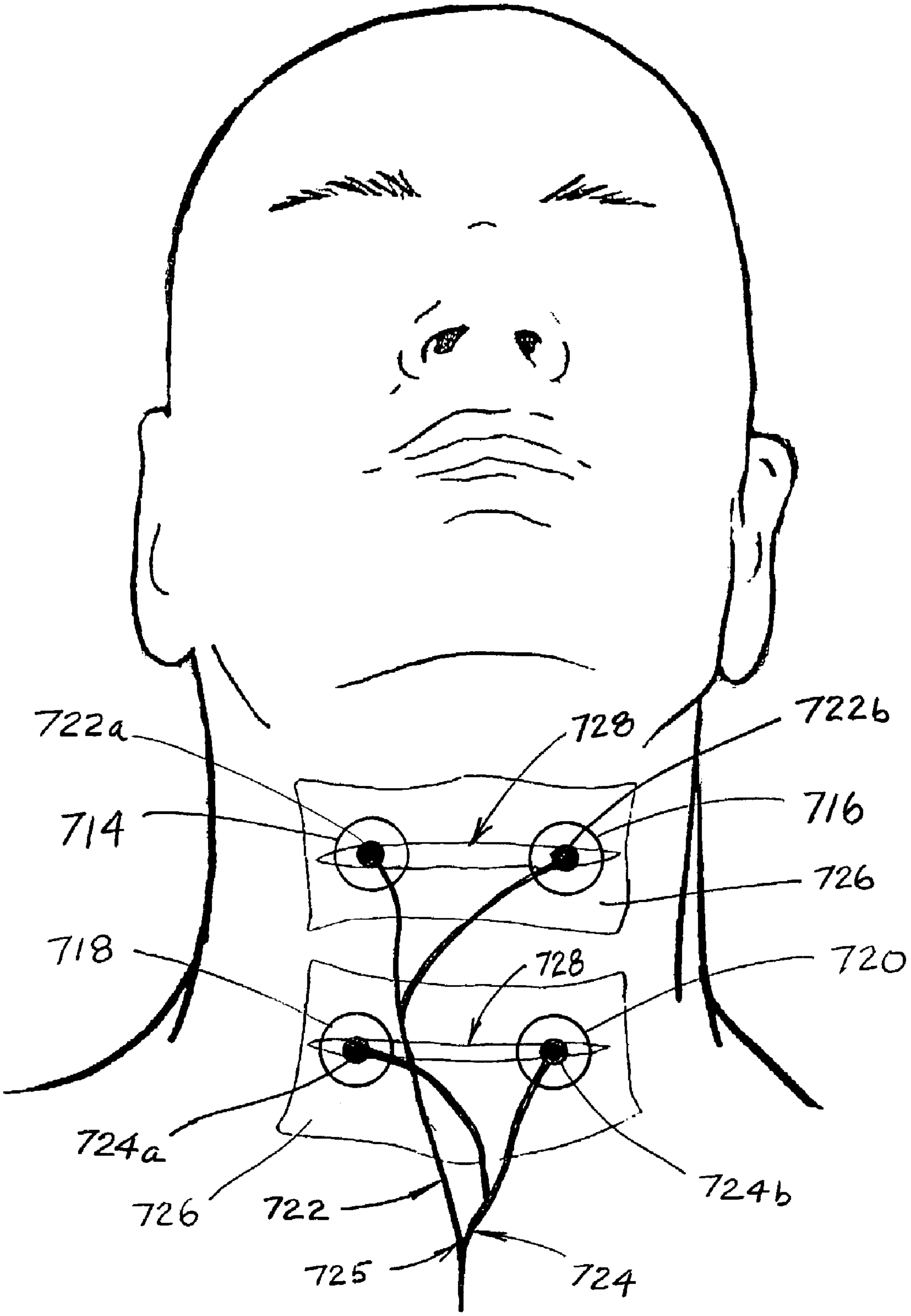
FIG. 7B illustrates the placement of an arrangement of electrodes similar to that of FIG. 7A on the throat of a patient according to a preferred embodiment of the invention.

Another arrangement of electrodes, in two horizontal pairs is illustrated in FIG. 7B. As shown therein, a first pair of electrodes 714 and 716 are placed horizontally immediately above the thyroid notch. A second pair of electrodes 718 and 720 are placed horizontally below the notch. The first pair of electrodes of this array is independently coupled, through an output jack, (not shown in FIG. 7B) to an output of switching network 602 (shown in FIG. 6) by lead wire 722, comprised of a pair of electrode connection ends 722*a* and 722*b* and an output jack end (not shown). The second pair of electrodes of this array is independently coupled, through an output jack, (not shown in FIG. 7B) to an output of switching network 602 (shown in FIG. 6) by lead wire 724, comprised of a pair of electrode connection ends 724*a* and 724*b* and an output jack end (not shown). As a result, each of these pairs of electrodes independently receives one or more series of electrical pulses generated by one or more of pulse generators 603–606 via switching network 602 as determined by microprocessor 601. Microprocessor 601 controls the switching operation of switching network 602 to control which output or outputs from pulse generators 603–606 are provided to each electrode in this electrode array. As shown in FIG. 7B, lead wires 722 and 724 may be mechanically joined together for ease in handling at junction 725.

A pair of adhesively backed tape overlays 726 are provided to secure the electrodes to the skin of the patient. Tape overlay 726 (also shown in FIGS. 7C, 7D, 7E and 9) is preferably provided with a shape that will allow it to conform closely to the skin of the patient's neck in either the horizontal orientation shown in FIGS. 7B and 7C or the vertical orientation shown in FIGS. 7D and 7E. Tape overlay 726 is also preferably provided with an outer surface that does not absorb moisture and a centrally located slot 728 that may be aligned over the connectors of the snap eyelets for the preferred electrodes. This slot permits the electrodes to placed on the skin of the patient's neck and secured with the tape overlay before connection the lead wires to the electrodes.

The arrangement of electrodes illustrated in FIG. 7B is suitable for most laryngeal and pharyngeal motor defects. A similar arrangement (not shown) in which the first pair of electrodes 714 and 716 are placed slightly higher on the throat may be employed if it is desired to stimulate the tongue and upper pharyngeal muscles to promote swallowing.

Figure 7C:
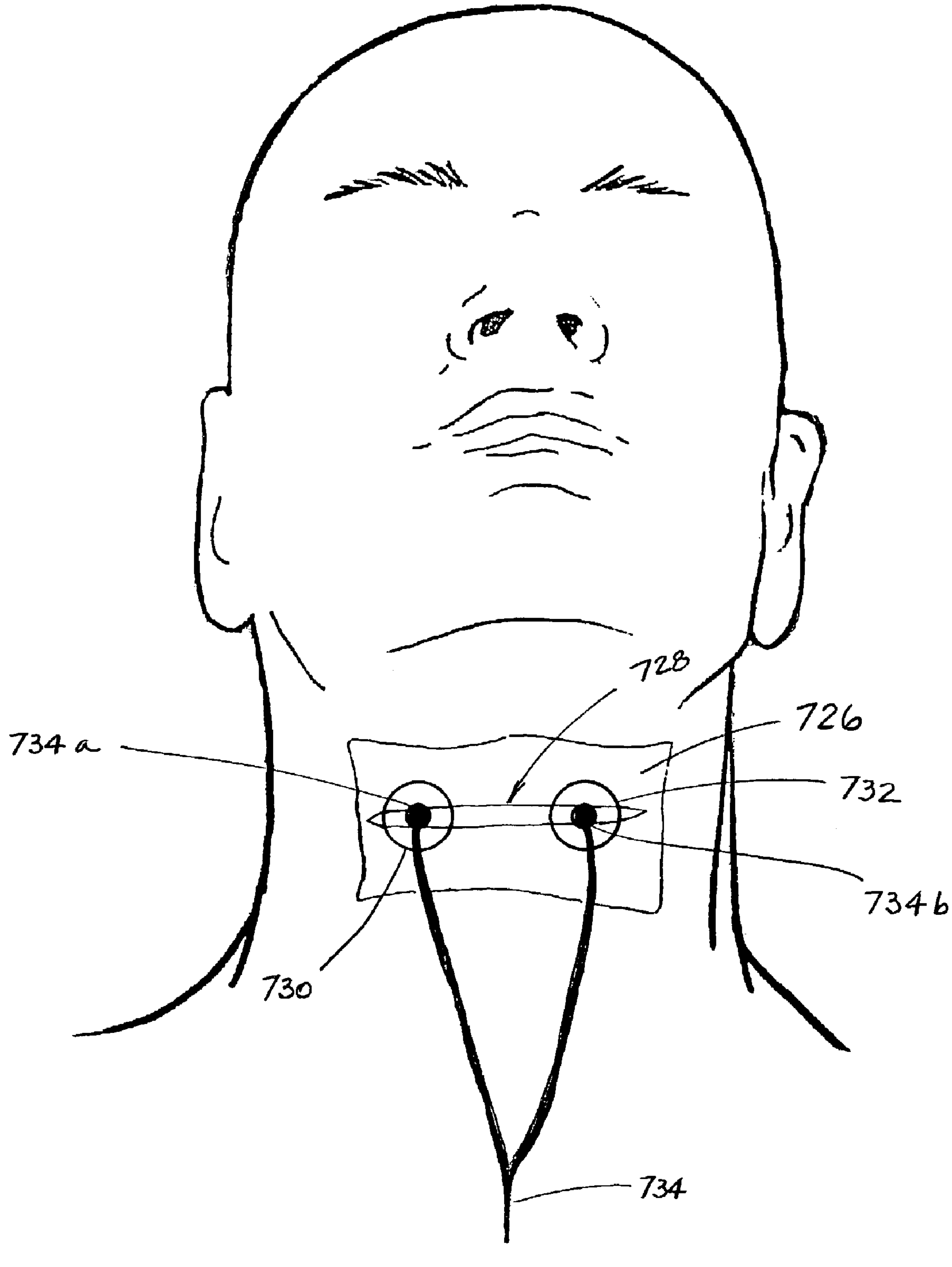
FIG. 7C illustrates the placement of two pairs of electrodes on the throat of a patient according to a preferred embodiment of the invention.

Another arrangement of electrodes, in a single horizontally disposed pair, is illustrated in FIG. 7C. This arrangement is also suitable for treatment of most laryngeal and pharyngeal motor defects. As shown in FIG. 7C, electrodes 730 and 732 are placed horizontally immediately above the thyroid notch. This pair of electrodes is independently coupled, through an output jack, (not shown in FIG. 7C) to an output of switching network 602 (shown in FIG. 6) by lead wire 734, comprised of a pair of electrode connection ends 734*a* and 734*b* and an output jack end (not shown). As a result, this pair of electrodes independently receives one or more series of electrical pulses generated by one or more of pulse generators 603–606 via switching network 602 as determined by microprocessor 601. Microprocessor 601 controls the switching operation of switching network 602 to control which output or outputs from pulse generators 603–606 are provided to each electrode in this electrode array. Also as shown in FIG. 7C, an adhesively backed tape overlay 726 having a central slot 728 is provided to secure the electrodes to the skin of the patient.

Figure 7D:
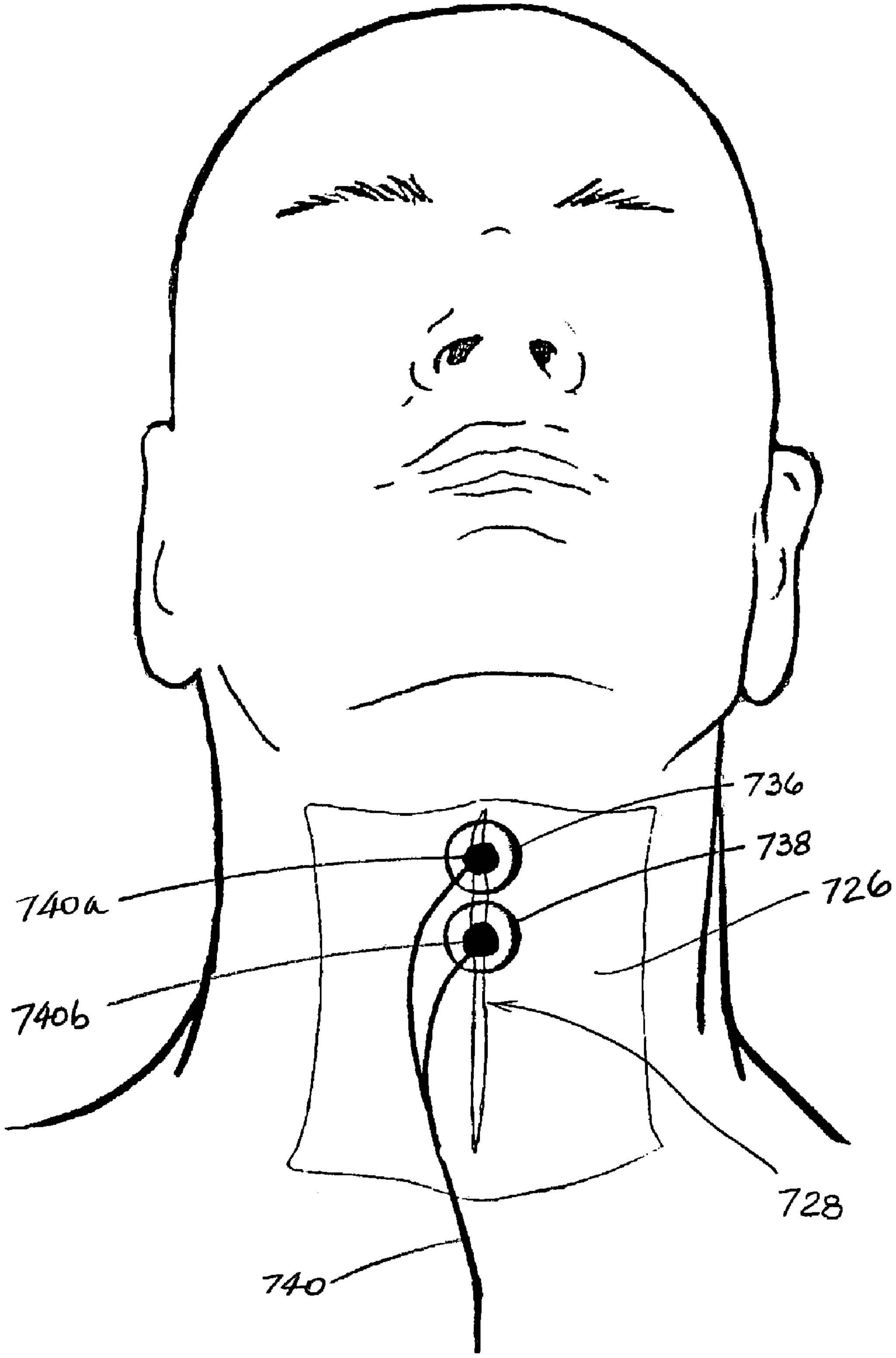
FIG. 7D illustrates the placement of a pair of electrodes in a vertical arrangement on the throat of a patient according to a preferred embodiment of the invention.

FIG. 7D illustrates another arrangement of electrodes that is suitable for treatment of most laryngeal and pharyngeal motor defects. As shown therein, electrodes 736 and 738 are both placed above the thyroid notch in a vertical arrangement, generally on the centerline of the throat. This pair of electrodes is independently coupled, through an output jack, (not shown in FIG. 7D) to an output of switching network 602 (shown in FIG. 6) by lead wire 740, comprised of a pair of electrode connection ends 740*a* and 740*b* and an output jack end (not shown). As a result, this pair of electrodes independently receives one or more series of electrical pulses generated by one or more of pulse generators 603–606 via switching network 602 as determined by microprocessor 601. Microprocessor 601 controls the switching operation of switching network 602 to control which output or outputs from pulse generators 603–606 are provided to each electrode in this electrode array. Also as shown in FIG. 7D, an adhesively backed tape overlay 726 having a central slot 728 is provided to secure the electrodes to the skin of the patient.

Figure 7E:
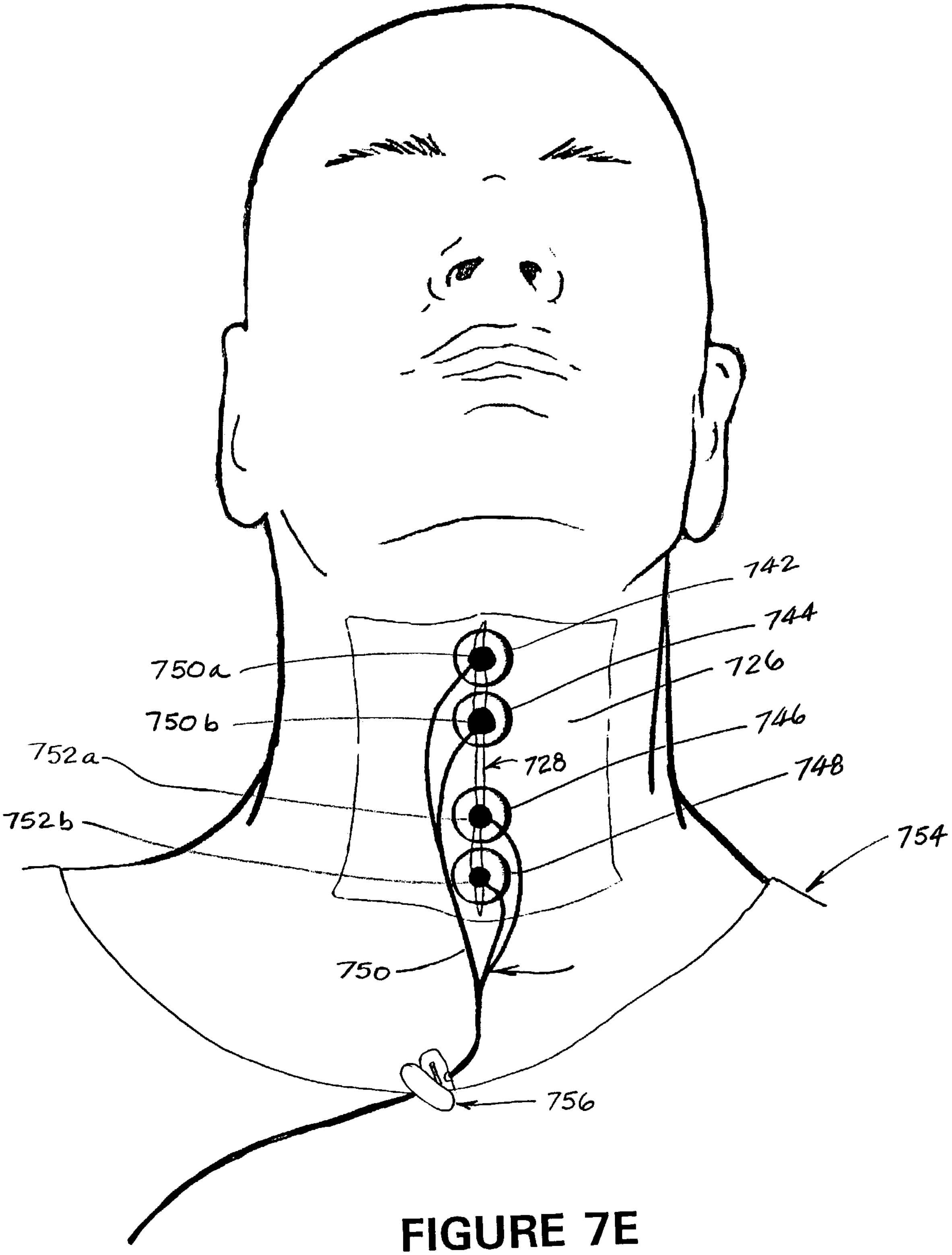
FIG. 7E illustrates the placement of two pairs of electrodes in a vertical arrangement on the throat of a patient according to a preferred embodiment of the invention.

FIG. 7E illustrates another arrangement of electrodes, in two pairs of vertically disposed electrodes. This arrangement is suitable for treatment of most laryngeal and pharyngeal motor defects and preferred for treatment of many such defects. In this arrangement, the four electrodes are positioned in a vertical row directly adjacent to one another, but not overlapping, starting with a first uppermost electrode being positioned on the patient's digastric muscles, covering the hyoid and the strap muscles of the patient's larynx, and ending with a fourth lowermost electrode being positioned at the base of the patient's thyroid cartilage. As shown in FIG. 7E, a first pair of electrodes 742 and 744 are placed vertically above the thyroid notch and generally along the centerline of the patient's throat. A second pair of electrodes 746 and 748 are placed vertically below the notch and generally along the same centerline as the first pair. The first pair of electrodes of this array is independently coupled, through an output jack, (not shown in FIG. 7D) to an output of switching network 602 (shown in FIG. 6) by lead wire 750, comprised of a pair of electrode connection ends 750*a* and 750*b* and an output jack end (not shown). The second pair of electrodes of this array is independently coupled, through an output jack, (not shown in FIG. 7D) to an output of switching network 602 (shown in FIG. 6) by lead wire 752, comprised of a pair of electrode connection ends 752*a* and 752*b* and an output jack end (not shown). As a result, each of these pairs of electrodes independently receives one or more series of electrical pulses generated by one or more of pulse generators 603–606 via switching network 602 as determined by microprocessor 601. The two upper electrodes 742 and 744 are coupled to a first output channel of the switching network 602, and the two lower electrodes 746 and 748 are coupled to a second output channel of the switching network 602.

Figure 11:
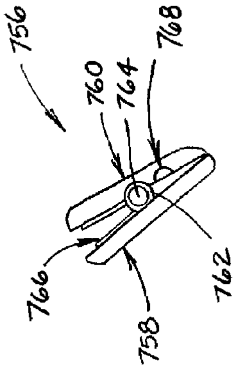
FIG. 11 is a side view of a preferred clip that forms a part of a preferred embodiment of the invention.

Microprocessor 601 controls the switching operation of switching network 602 to control which output or outputs from pulse generators 603–606 are provided to each electrode in this electrode array. As shown in FIG. 7D, an adhesively backed tape overlay 726 is provided to secure the electrodes to the skin of the patient. In addition, lead wires 750 and 752 may be mechanically joined together for ease in handling, and clipped to patient's shirt 754 using preferred clip 756. As shown in more detail in FIG. 11, clip 756 is comprised of first clip portion 758 and second clip portion 760. The first clip portion has an integral ring 762 in which pin 764 of the second clip portion may rotate. Spring 766 is provided between the clip portions to keep the clip "closed", yet allow it to be easily opened. A lead wire slot 768 is provided in clip portion 760 to retain the lead wire so that it may be clipped to an item of the clothing of the patient and thereby retained securely in place.

Figure 3:
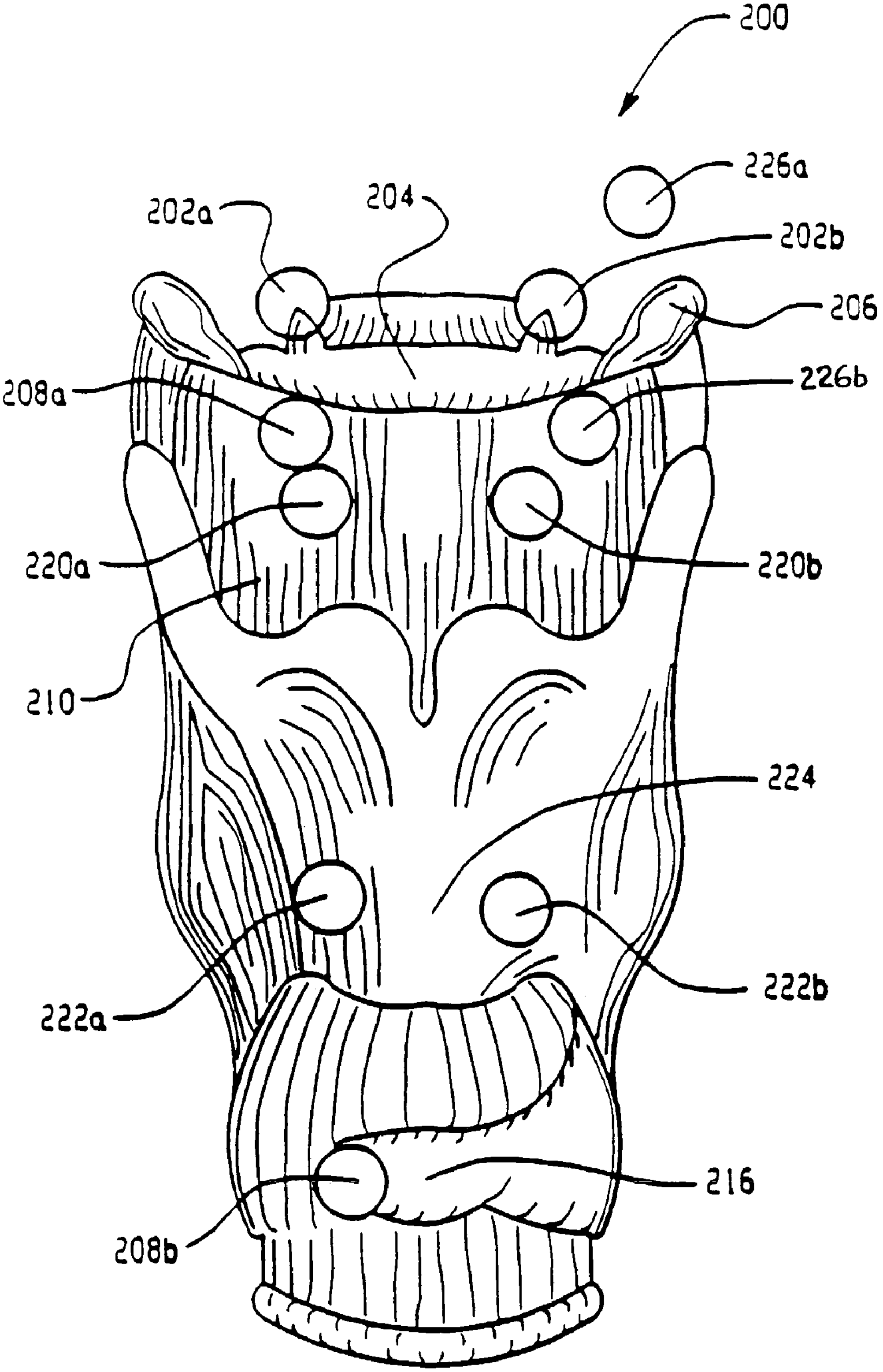
FIG. 3 is a view of a portion a pharyngeal region of a patient illustrating several exemplary placements of a pair of electrodes according to the present invention.
Figure 4:
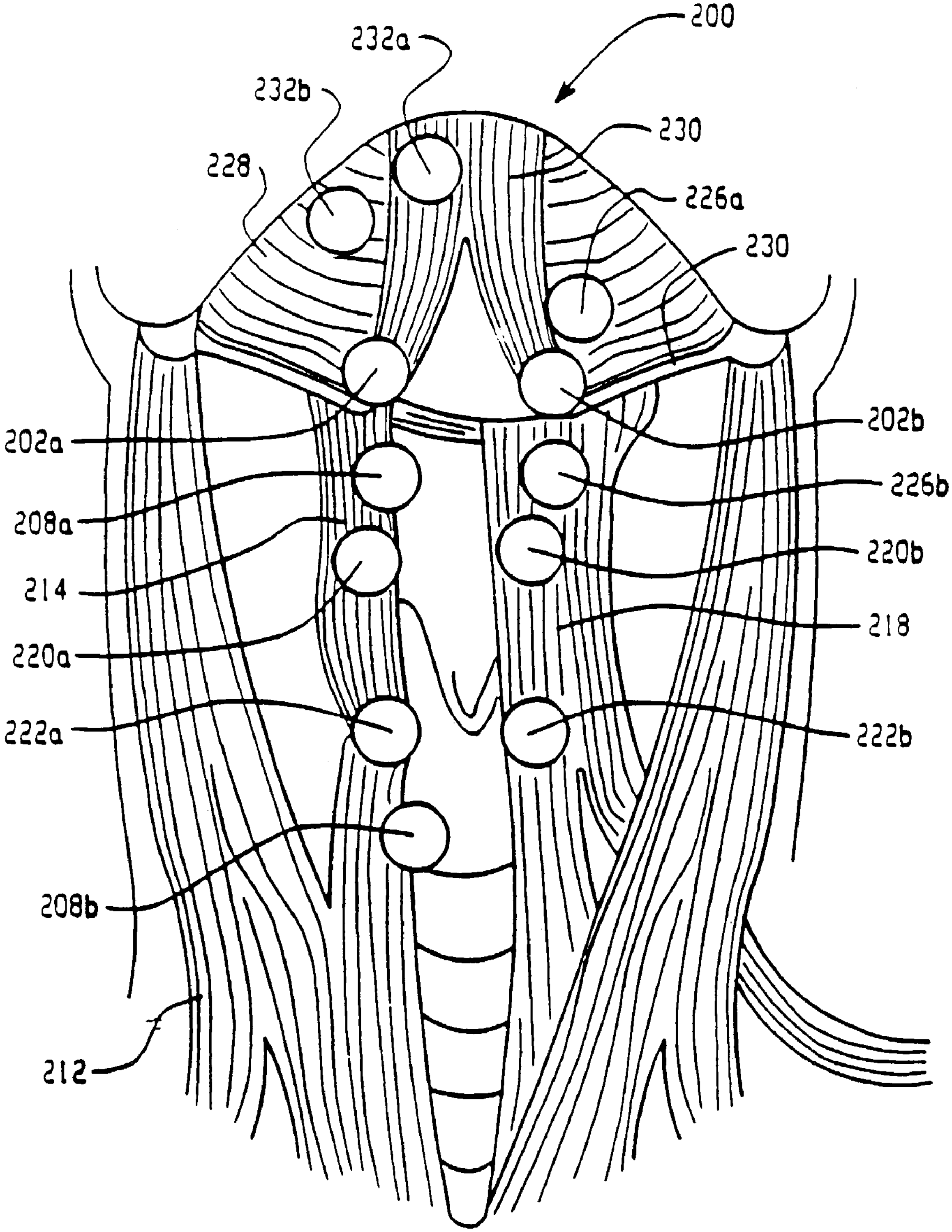
FIG. 4 is a view of a portion a pharyngeal region of a patient illustrating several exemplary placements of a pair of electrodes according to the present invention.

The electrode arrangements of FIGS. 7A–7E are provided as examples of electrode placement and are not intended to limit the number and arrangement of electrodes for use in practicing the present invention. The electrodes are selectively placed in any suitable site within the pharyngeal region 200 of the patient as shown in FIGS. 3 and 4. The placement of the electrodes in the pharyngeal region of the patient is based on several factors, such as the extent and type of oropharyngeal disorder exhibited by the patient and, given the extent and type of oropharyngeal disorder exhibited, those locations within the pharyngeal region, that when subjected to electrical stimulus, have the possibility of eliciting the strongest and most complete swallow. An evaluation for swallowing ability is done on the patient to determine the extent and type of oropharyngeal disorder. The critical elements in the evaluation are analysis by video fluoroscopy and clinical evaluation to determine the presence of a gag reflex, a dry swallow, and ability to tolerate one's own secretions. The placement of the electrodes may be changed several times in an effort to obtain the strongest and most effective treatment.

As shown in FIGS. 3 and 4, in a two-electrode embodiment of the present invention, a pair of electrodes 202*a* and 202*b* may be positioned on the skin of the pharyngeal region 200 at approximately the position of the lesser horn 204 of the hyoid bone 206 on either side of the pharyngeal region 200 and just above the body of the hyoid bone 206. The electrodes overlie the muscles of the floor of the mouth (not shown). In an alternative two-electrode embodiment of the present invention, a pair of electrodes 208*a* and 208*b* may be positioned on the side of the pharyngeal region 200 on one side of the midline of the pharyngeal region 200. One electrode 208*a* is placed on the thyrohyoid membrane 210 at approximately the level of the lesser horn 204 close to the hyoid bone 206. This electrode 208*a* overlies the sternothyroid muscle 212 and the thyrohyoid muscle 214. The other electrode 208*b* is placed on the cricoid cartilage 216 to the side of the midline of the pharyngeal region 200. This electrode overlies the sternothyroid muscle 218 and the sternothyroid muscle 212 on one side of the midline of the pharyngeal region. In yet another embodiment of the present invention, a pair of electrodes 220*a* and 220*b* may be positioned on the skin of the pharyngeal region 200 on the thyrohyoid membrane 210 on either side of the midline of the pharyngeal region 200. These electrodes overlie the thyrohyoid muscle 214 and the sternothyroid muscle 218. In another embodiment of the present invention, a pair of electrodes 222*a* and 222*b* may be positioned on the skin of the pharyngeal region 200 on either side of the midline of the pharyngeal region 200 proximately midway between the thyroid notch 224 and the cricoid cartilage 216. These electrodes overlie the sternothyroid muscle 218 and the transition zone between the sternothyroid muscle 212 and the thyrohyoid muscle 214 on either side of the midline of the pharyngeal region 200.

In an additional embodiment of the present invention, a pair of electrodes 226*a* and 226*b* may be positioned on the skin of the pharyngeal region 200 on one side of the midline of the pharyngeal region 200. One electrode 226*a* is placed just lateral to the lesser horn 204 of the hyoid bone 206 proximately midway between the hyoid bone 206 and the lower border of the mandible (not shown). This electrode overlies the mylohyoid muscle 228 and the digastric muscle 230. The other electrode 226*b* is placed proximate to the upper end of the thyrohyoid membrane 210 and proximate to the hyoid bone 206 or on the hyoid bone 206 proximately at the level of the lesser horn 204 of the hyoid bone 206. This electrode overlies the sternothyroid muscle 212 and the thyrohyoid muscle 214. In a further embodiment of the present invention (FIG. 4), a pair of electrodes 232*a* and 232*b* may be positioned on the skin of the pharyngeal region 200 to the side of the midline of the pharyngeal region 200. One electrode 232*a* is placed on the midline of the pharyngeal region near the chin (not shown). The other electrode 232*b* is placed laterally to the other electrode. These electrodes overlie the mylohyoid muscle 228 and the digastric muscle 230 in the midline and to one side of the midline of the pharyngeal region 200. In general, the placement and dimensions of the electrodes in accordance with the present invention is performed so as to avoid the carotid body and to insure the safety of the patient.

Figure 2:
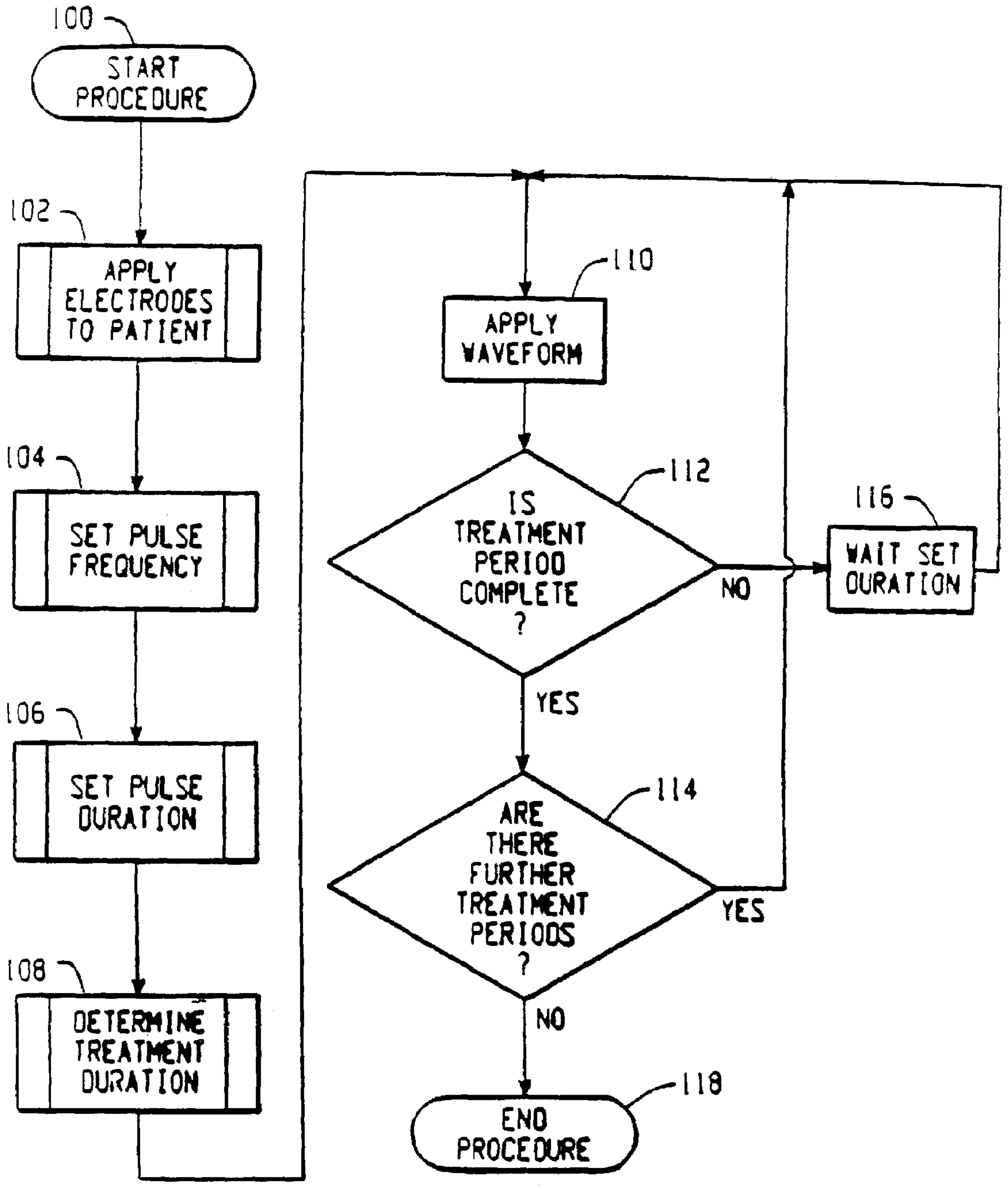
FIG. 2 is a flow chart of a method for electrical pharyngeal neuromuscular stimulation according to the present invention for promoting swallowing.

A preferred method for electrical pharyngeal neuromuscular stimulation using the apparatus shown in FIG. 1 will now be described with reference to FIG. 2. At Start Procedure step 100, the procedure for treating oropharyngeal disorders with electrical stimulation is initiated. Next, at Apply Electrodes To Patient step 102, electrodes are applied to the pharyngeal area of a patient, as described hereinabove. At Set Pulse Frequency step 104, a pulse frequency is set in accordance with the parameters disclosed above. Similarly, at Set Pulse Duration step 106, pulse duration is set. Finally, at Determine Treatment Time step 108, a determination of a treatment duration is made, as well as to the number of treatment periods that are to be applied.

At Apply Waveform step 110, an actual waveform associated with the previously selected parameters is applied to the pharyngeal area of a patient. Next, at Decision step 112, a determination is made as to whether a treatment period is complete in accordance with the preselected standards. A positive determination causes progress to Decision step 114 and a negative determination causes progress to Wait For Duration step 116. At Wait For Duration step 116, the device automatically waits for a predetermined period of time before returning to Apply Waveform step 110. At Decision step 114, a determination is made as to whether further treatment periods are merited. A positive determination causes a return to Wait Set Duration step 110. A negative determination results in completion of the treatment procedure as indicated by End Procedure step 118.

Figure 8:
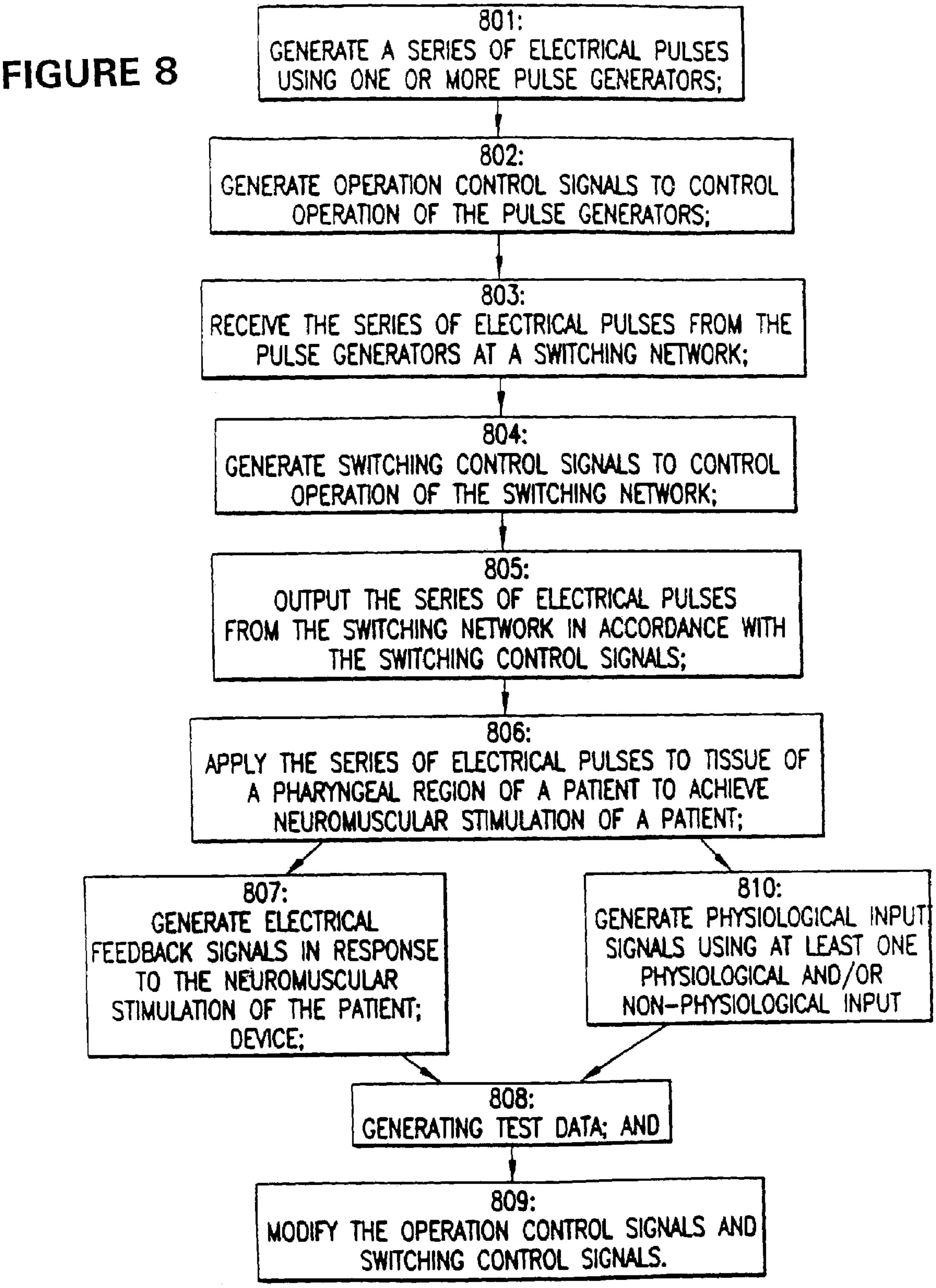
FIG. 8 is a diagram of an alternative method for electrical neuromuscular stimulation according to the present invention for promoting swallowing.

With reference to FIG. 8, an alternative embodiment of a preferred method for electrical pharyngeal neuromuscular stimulation according to the present invention includes the steps of:

801: generating a series of electrical pulses using one or more pulse generators;

802: generating operation control signals to control operation of the pulse generators;

803: receiving the series of electrical pulses from the pulse generators at a switching network;

804: generating switching control signals to control operation of the switching network,

805: outputting the series of electrical pulses from the switching network in accordance with the switching control signals;

806: applying the series of electrical pulses to tissue of a pharyngeal region of a patient using an electrode array to achieve neuromuscular stimulation of a patient;

807: generating electrical feedback signals in response to the neuromuscular stimulation of the patient;

808: generating test data in response to the electrical feedback signals; and

809: modifying the operation control signals and switching control signals in response to the electrical feedback signals.

This method may further include the step of:

810: generating physiological and/or non-physiological input signals using at least one physiological and/or non-physiological input device.

When step 810 is included, the test data generated in step 808 above is also based upon the physiological and/or non-physiological input signals. Similarly, step 809 above includes modification of the operation control signals and switching of control signals in response to both the electrical feedback signals and the physiological and/or non-physiological input signals.

The preferred method depicted in FIG. 8 may optionally include the steps of monitoring the electrical feedback signals, the physiological input signals, the non-physiological input signals, or any combination thereof and downloading the test data to a test data receiver such as, for example, an external receiving device.

The practice of various embodiments of the method according to the present invention will now be described in further detail. In the following examples, the inventive method was used to treat dysphagia. These examples are not intended to limit the scope of the present invention.

EXAMPLE 1

One hundred and ninety-five patients suffering from dysphagia as a result of a stroke or neurodegeneration were studied. The swallowing ability of each patient was evaluated to determine the extent and type of dysphagia exhibited by the patient. The swallowing ability of each patient was assigned a number which corresponds to a defined swallow state wherein the swallow states are listed below:

swallow state zero is the inability to have a pharyngeal contraction;

swallow state one is the ability to swallow one's own secretions;

swallow state two is the ability to swallow paste, pudding, or similar substances;

swallow state three is the ability to swallow honey or similar substances;

swallow state four is the ability to swallow nectar or similar substances;

swallow state five is the ability to swallow liquids; and swallow state six is the ability to swallow water.

All of the patients were determined to have swallowing states of either zero or one, indicating the patient did not have a complete pharyngeal contraction and had no gag reflex or ability to handle secretions. The patients were then subjected to a series of treatment sessions. The patients were divided into two treatment groups: electrical stimulation and thermal stimulation.

Sixty three patients underwent a series of electrical stimulation treatment sessions. Preferably, the patients underwent a least seven electrical stimulation treatment sessions. In each treatment session, electrodes such as are described herein and illustrated in FIGS. 7 and 7A were selectively placed on the skin of the pharyngeal region of the patient. The placement of the electrodes was determined by the extent and type of dysphagia exhibited by the patient and, given the extent and type of dysphagia exhibited, those locations within the pharyngeal region, when subjected to electrical stimulus, have the possibility of eliciting the strongest and most complete swallow. Electrode placement was adjusted until the patient achieved the most complete swallowing contraction for which he was capable. Once the correct electrode placement was determined, the intensity of the current was increased by small increments until the tolerance and comfort level limits are reached in the patient. The optimal intensity was realized when the patient felt a tugging or pinch in the area of stimulation. The patient was then subjected to continuous electrical stimulation wherein electric pulses were continuously generated and delivered to the electrodes until a complete swallow was achieved or the tolerance level was reached in the patient. This step was repeated five to twenty times in each treatment session wherein the patient was subjected to continuous electrical stimulation. If the electrical stimulation was successful in promoting a complete contraction, swabbing of the oral cavity was done and the patient attempted a dry swallow. In those patients who did not exhibit any pharyngeal contraction, one or more treatment sessions were required before an adequate dry swallow occurred.

Once an adequate dry swallow was achieved, oral intake was provided to assist in the treatment. The consistency of the oral intake was determined by the strength of the contraction elicited by the patient. If the patient was able to swallow his own saliva, swabbing the oral cavity with a sponge moistened by water or juice was performed. The patient attempted to swallow the water or juice while subjected to continuous electrical stimulation. Once the patient had achieved audible, strong contractions, the patient was challenged with pudding, thick liquid, or ice slush. The patient attempted to swallow these substances while subjected to continuous electrical stimulation. Once three to five strong swallows were achieved with the assistance of electrical stimulation, the patient attempted to swallow these substances without the assistance of electrical stimulation. Treatment sessions continued with each patient until the patient's improvement reached a plateau.

Thirty-one patients were subjected to a series of thermal stimulation treatment sessions. Preferably, the patients were subjected to a least seven thermal stimulation treatment sessions. In each treatment session, a mirror or probe was immersed in ice or cold substance. The tonsillar fossa was stimulated with the mirror or probe. The patient then closed his mouth and attempted a dry swallow. If the stimulation was successful in promoting a complete contraction, oral intake was provided to assist in the treatment. The consistency of the oral intake was determined by the strength of the contraction elicited by the patient. Once an adequate dry swallow was achieved, oral intake was provided to assist in the treatment. The consistency of the oral intake was determined by the strength of the contraction elicited by the patient. If the patient was able to swallow his own saliva, swabbing the oral cavity with a sponge moistened by water or juice was performed. The patient attempted to swallow the water or juice while subjected to thermal stimulation. Once the patient had achieved audible, strong contractions, the patient was challenged with pudding, thick liquid or ice slush. The patient attempted to swallow these substances while subjected to thermal stimulation. Once three to five strong swallows were achieved with the assistance of thermal stimulation, the patient attempted to swallow these substances without the assistance of thermal stimulation. Treatment sessions continued with each patient until the patient's improvement plateaued.

Figure 5:
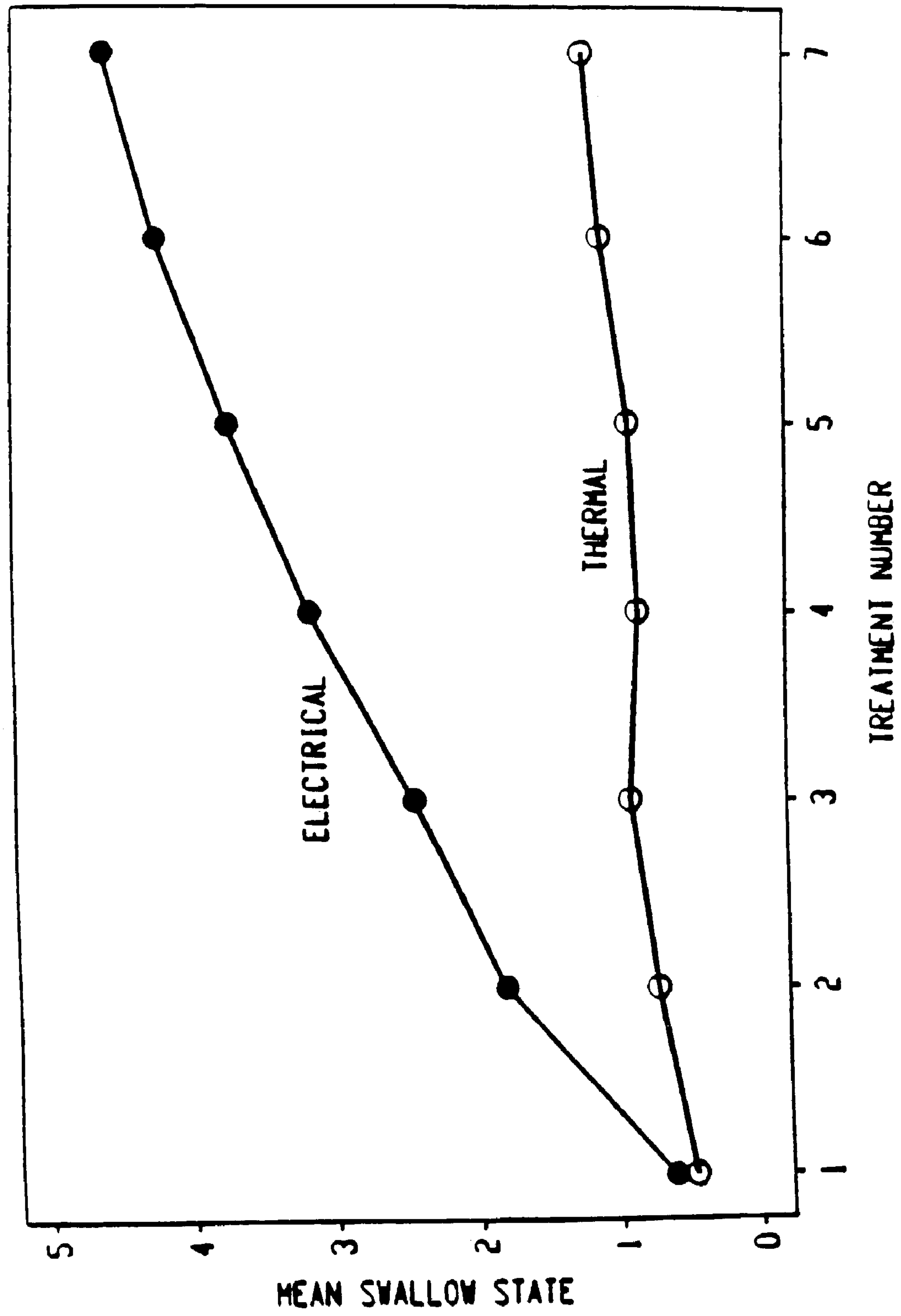
FIG. 5 is a graph illustrating the effectiveness of the electrical neuromuscular stimulation method and apparatus of the present invention.

The effectiveness of the electrical stimulation treatments and the thermal stimulation treatments is shown in FIG. 5, a graph illustrating the mean swallowing state achieved after electrical stimulation treatment sessions and thermal stimulation treatments. After seven treatment sessions, the mean swallowing state of the patients treated with electrical stimulation was swallow state five, or the ability to swallow thin liquids. After seven treatment sessions, the mean swallowing state of the patients treated with thermal stimulation was only swallow state one, or the ability to handle one's own secretions.

The method and apparatus for electrical pharyngeal neuromuscular stimulation of the present invention provides an effective and non-invasive treatment for dysphagia. The method and apparatus for electrical pharyngeal neuromuscular stimulation is more effective for treating dysphagia than traditional treatment methods, such as thermal stimulation. Further, the method and apparatus of the present invention is effective for treating worst-case dysphagia resulting from neurodegeneration and strokes.

While various embodiments of a method and device for treating oropharyngeal disorders with electrical stimulation have been disclosed, it should be understood that modifications and adaptations thereof will occur to persons having ordinary skill in the art to which the invention relates. Other features and aspects of this invention will be appreciated by those having such skill in the art upon reading and comprehending this disclosure. Such features, aspects, and expected variations and modifications of the reported results and examples, as well as their equivalents, are clearly within the scope of the invention as described by the following claims.

What is claimed is:

1. A method of electrical neuromuscular stimulation for treating oropharyngeal disorders in a patient, said method comprising the steps of:

(a) providing a first electrode and a second electrode, each of which comprises:
   (i) a snap eyelet having a first side and a second side, said second side having a connector to which a lead wire may be attached;
   (ii) a conductive film that is attached to the first side of the snap eyelet;
   (iii) an adhesive and conductive gel layer that is attached to the conductive film and adapted to be attached to the skin of the patient;

(b) providing at least one adhesively backed tape overlay for securing the first and second electrodes to the skin of the patient;

(c) providing a pulse generator for generating a series of electrical pulses, said pulse generator further comprising:
   (i) a frequency controller for modulating an electrical signal generated by the pulse generator at a predetermined frequency to produce the series of electrical pulses;
   (ii) a duration control circuit for controlling the duration of time for which said pulse generator generates the series of electrical pulses; and
   (iii) an intensity control circuit for regulating the series of electrical pulses such that the electrical current does not exceed a predetermined current or voltage value;
   (iv) an output jack for connection of a lead wire;

(d) providing at least one lead wire having an electrode connection end and an output jack end, wherein said electrode connection end is adapted to be attached to a connector of a snap eyelet, and wherein said output jack end is adapted to be attached to the output jack of the pulse generator;

(e) placing the first electrode on the skin of the patient's throat with the adhesive gel layer in contact with the skin;

(f) placing the second electrode on the skin of the patient's throat with the adhesive gel layer in contact with the skin;

(g) securing the electrodes to the skin of the patient's throat by application of at least one adhesively backed tape overlay to the skin of the patient's throat over at least a portion of each of the electrodes;

(h) attaching a lead wire to the snap eyelet of each electrode and to the output jack of the pulse generator so as to electrically connect the snap eyelet of each electrode to the output jack;

(i) generating a series of electrical pulses using the pulse generator so as to apply the series of electrical pulses to the patient's throat using the electrodes.

2. The method of claim 1 which includes the following steps:

(j) providing a clip that is adapted to secure a lead wire to an item of clothing of the patient;

(k) securing the lead wire to the item of clothing of the patient using the clip.

3. The method of claim 1 which includes the following steps instead of the corresponding steps of claim 1:

(b) providing an adhesively backed tape overlay having a centrally located slot therethrough;

(g) applying the adhesively backed tape overlay to the patient's skin over the first and second electrodes with the slot aligned with the connectors of the snap eyelets.

4. The method of claim 1 which includes the following step instead of step (d) of claim 1:

(d) providing a lead wire having a first electrode connection end, a second electrode connection end and an output jack end, wherein each of said electrode connection ends is adapted to be attached to a connector of a snap eyelet, and wherein said output jack end is adapted to be attached to the output jack of the pulse generator;

and which includes the following steps instead of step (h) of claim 1:

(h1) attaching the first electrode connection end of the lead wire to the snap eyelet of the first electrode;

(h2) attaching the second electrode connection end of the lead wire to the snap eyelet of the second electrode;

(h3) attaching the output jack end of the lead wire to the output jack of the pulse generator.

5. The method of claim 1 which includes the following steps instead of the corresponding steps of claim 1:

(e) placing the first electrode on the skin of the patient's throat above the thyroid notch and generally on the centerline of the throat with the adhesive gel layer in contact with the skin;

(f) placing the second electrode on the skin of the patient's throat below the first electrode and above the thyroid notch and generally on the centerline of the throat with the adhesive gel layer in contact with the skin.

6. The method of claim 1 which includes the following step instead of the corresponding step of claim 1:

(a) providing a first electrode and a second electrode, each of which comprises:

(i) a snap eyelet having a first side and a second side, said second side having a connector to which a lead wire may be attached;

(ii) a conductive film having a first side and a second side, said first side being attached to the first side of the snap eyelet;

(iii) an adhesive and conductive gel layer that is attached to the conductive film and adapted to be attached to the skin of the patient;

(iv) an electrically-insulating layer that is attached to the second side of the conductive film.

7. The method of claim 1 which includes the following step instead of the corresponding step of claim 1:

(a) providing a first electrode and a second electrode, each of which comprises:

(i) a snap eyelet having a first side and a second side, said first side being generally circular and having a diameter of approximately 7 mm and said second side having a stud connector to which a lead wire may be attached;

(ii) a generally circular conductive carbon film having a diameter within the range of 16 mm–22 mm that is attached to the first side of the snap eyelet;

(iii) an adhesive and conductive gel layer that is attached to the conductive film and adapted to be attached to the skin of the patient.

8. The method of claim 1 which includes the following steps instead of the corresponding steps of claim 1:

(a) providing a first electrode, a second electrode, a third electrode and a fourth electrode, each of which comprises:

(i) a snap eyelet having a first side and a second side, said second side having a connector to which a lead wire may be attached;

(ii) a conductive film that is attached to the first side of the snap eyelet;

(iii) an adhesive and conductive gel layer that is attached to the conductive film and adapted to be attached to the skin of the patient;

(c) providing a pulse generator for generating a series of electrical pulses, said pulse generator further comprising:

(i) a frequency controller for modulating an electrical signal generated by the pulse generator at a predetermined frequency to produce the series of electrical pulses;

(ii) a duration control circuit for controlling the duration of time for which said pulse generator generates the series of electrical pulses; and (iii) an intensity control circuit for regulating the series of electrical pulses such that the electrical current does not exceed a predetermined current or voltage value;

(iv) a first output jack and a second output jack, each of which is adapted for connection of a lead wire;

and which includes the following steps instead of step (d) of claim 1:

(d1) providing a first lead wire having a first electrode connection end that is adapted to be connected to the connector of the snap eyelet of the first electrode, a second electrode connection end that is adapted to be connected to the connector of the snap eyelet of the second electrode, and an output jack end that is adapted to be attached to an output jack of the pulse generator;

(d2) providing a second lead wire having a third electrode connection end that is adapted to be connected to the connector of the snap eyelet of the third electrode, a fourth electrode connection end that is adapted to be connected to the connector of the snap eyelet of the fourth electrode, and an output jack end that is adapted to be attached to an output jack of the pulse generator;

and which includes the following steps instead of step (e) of claim 1:

(e1) placing the first electrode on the skin of the patient's throat above the thyroid notch and generally on the centerline of the throat with the adhesive gel layer in contact with the skin;

(f2) placing the second electrode on the skin of the patient's throat above the thyroid notch, below the first electrode, and generally on the centerline of the throat with the adhesive gel layer in contact with the skin;

and which includes the following steps instead of step (f) of claim 1:

(f1) placing the third electrode on the skin of the patient's throat below the thyroid notch and generally on the centerline of the throat with the adhesive gel layer in contact with the skin;

(f2) placing the fourth electrode on the skin of the patient's throat below the thyroid notch, below the third electrode, and generally on the centerline of the throat with the adhesive gel layer in contact with the skin;

and which includes the following steps after step (g) instead of steps (h) and (i) of claim 1:

(h) attaching the first electrode connection end of the first lead wire to the connector of the snap eyelet of the first electrode;

(i) attaching the second electrode connection end of the first lead wire to the connector of the snap eyelet of the second electrode;

(j) attaching the third electrode connection end of the second lead wire to the connector of the snap eyelet of the third electrode;

(k) attaching the fourth electrode connection end of the second lead wire to the connector of the snap eyelet of the fourth electrode;

(l) attaching the output jack end of first lead wire to first output jack of the pulse generator;

(m) attaching the output jack end of second lead wire to second output jack of the pulse generator;

(n) generating a series of electrical pulses using the pulse generator so as to apply the series of electrical pulses to the patient's throat using the electrodes.

9. The method of claim 8 which includes the following step instead of the corresponding step of claim 8:

(a) providing a first electrode, a second electrode, a third electrode and a fourth electrode, each of which comprises:

(i) a snap eyelet having a first side and a second side, said second side having a connector to which a lead wire may be attached;

(ii) a conductive film that is attached to the first side of the snap eyelet;

(iii) an adhesive and conductive gel layer that is attached to the conductive film and adapted to be attached to the skin of the patient;

wherein each electrode has a maximum electrical impedance of about 150 ohms.

10. The method of claim 8 which includes providing a pulse generator having an intensity control circuit for independently regulating:

(a) the current of the series of electrical pulses that are passed through the first output jack; and (b) the current of the series of electrical pulses that are passed through the second output jack.

11. The method of claim 10 which includes providing a pulse generator having an intensity control circuit for independently regulating:

(a) the current of the series of electrical pulses that are passed through the first output jack; and (b) the current of the series of electrical pulses that are passed through the second output jack;

so that the current of each pulse is within the range of 0.5 to 25 milliamps.

12. An apparatus for applying electrical neuromuscular stimulation to a patient for treatment of oropharyngeal disorders, said apparatus comprising:

(a) a first electrode and a second electrode, each of which comprises:

(i) a snap eyelet having a first side and a second side, said second side having a connector to which a lead wire may be attached;

(ii) a conductive film that is attached to the first side of the snap eyelet;

(iii) an adhesive and conductive gel layer that is attached to the conductive film and adapted to be attached to the skin of the patient;

(b) at least one adhesively backed tape overlay for securing the first and second electrodes to the skin of the patient;

(c) a pulse generator for generating a series of electrical pulses, said pulse generator comprising:

(i) a frequency controller for modulating an electrical signal generated by the pulse generator at a predetermined frequency to produce the series of electrical pulses;

(ii) a duration control circuit for controlling the duration of time for which said pulse generator generates the series of electrical pulses; and (iii) an intensity control circuit for regulating the series of electrical pulses such that the electrical current does not exceed a predetermined current or voltage value;

(iv) an output jack for connection of a lead wire;

(d) a lead wire having a first electrode connection end, a second electrode connection end and an output jack end, wherein each of said electrode connection ends is adapted to be attached to a connector of a snap eyelet, and wherein said output jack end is adapted to be attached to the output jack of the pulse generator.

13. The apparatus of claim 12 wherein the adhesively backed tape overlay has a centrally located slot therethrough, so that it may be applied to the patient's skin over the first and second electrodes with the slot aligned with the connectors of the snap eyelets.

14. The apparatus of claim 12 wherein each of the electrodes comprises:

(a) a snap eyelet having a first side and a second side, said second side having a connector to which a lead wire may be attached;

(b) a conductive film having a first side and a second side, said first side being attached to the first side of the snap eyelet;

(c) an adhesive and conductive gel layer that is attached to the conductive film and adapted to be attached to the skin of the patient;

(d) an electrically-insulating layer that is attached to the second side of the conductive film.

15. The apparatus of claim 12 which includes:

(a) a first electrode, a second electrode, a third electrode and a fourth electrode, each of which comprises:

(i) a snap eyelet having a first side and a second side, said second side having a connector to which a lead wire may be attached;

(ii) a conductive film that is attached to the first side of the snap eyelet;

(iii) an adhesive and conductive gel layer that is attached to the conductive film and adapted to be attached to the skin of the patient;

(b) a pulse generator having a first output jack and a second output jack, each of which is adapted for connection of a lead wire;

(c) a first lead wire having a first electrode connection end, a second electrode connection end and an output jack end, wherein said first electrode connection end is adapted to be connected to the connector of the first electrode, said second electrode connection end is adapted to be connected to the connector of the second electrode and said output jack end is adapted to be connected to the first output jack of the pulse generator.

(d) a second lead wire having a third electrode connection end, a fourth electrode connection end and an output jack end, wherein said third electrode connection end is adapted to be connected to the connector of the third electrode, said fourth electrode connection end is adapted to be connected to the connector of the fourth electrode and said output jack end is adapted to be connected to the second output jack of the pulse generator.

16. The apparatus of claim 15 wherein the pulse generator has an intensity control circuit for independently regulating:

(a) the current of the series of electrical pulses that are passed through the first output jack; and (b) the current of the series of electrical pulses that are passed through the second output jack.

17. The apparatus of claim 16 wherein the intensity control circuit independently regulates:

(a) the current of the series of electrical pulses that are passed through the first output jack; and (b) the current of the series of electrical pulses that are passed through the second output jack;

each within the range of 0.5 to 25 milliamps.

18. An electrode for use in applying electrical neuromuscular stimulation to a patient for treatment of oropharyngeal disorders, said electrode comprising:

(a) a snap eyelet having a first side and a second side, said first side being generally circular and having a diameter of about 7 mm and said second side having a stud connector to which a lead wire may be attached;

(b) a generally circular conductive film having a diameter within the range of 16 mm–22 mm that is attached to the first side of the snap eyelet;

(c) an adhesive and conductive layer of cross-linked hydrogel that is attached to the conductive film and adapted to be attached to the skin of the patient.

19. The electrode of claim 18 which includes an electrically-insulating layer that is attached to the second side of the conductive film.

20. The electrode of claim 18 which has a maximum electrical impedance of about 150 ohms.

* * * * *